(12) United States Patent
Ponce

(10) Patent No.: US 7,611,862 B2
(45) Date of Patent: *Nov. 3, 2009

(54) METHOD AND APPARATUS FOR DETECTING AND QUANTIFYING BACTERIAL SPORES ON A SURFACE

(75) Inventor: Adrian Ponce, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/332,788

(22) Filed: Jan. 12, 2006

(65) Prior Publication Data

US 2006/0292664 A1    Dec. 28, 2006

Related U.S. Application Data

(63) Continuation-in-part of application No. 10/987,202, filed on Nov. 12, 2004.

(60) Provisional application No. 60/740,805, filed on Nov. 30, 2005.

(51) Int. Cl.
   C12Q 1/06     (2006.01)
   C12Q 1/04     (2006.01)
   C12Q 1/00     (2006.01)
   C12M 1/34     (2006.01)

(52) U.S. Cl. .................. 435/34; 435/39; 435/31; 435/4; 435/287.1

(58) Field of Classification Search .................. 435/34, 435/39, 40.5, 40.51
   See application file for complete search history.

(56) References Cited

U.S. PATENT DOCUMENTS

| | | | |
|---|---|---|---|
| 4,560,665 A | 12/1985 | Nakae et al. | 436/172 |
| 4,943,522 A | 7/1990 | Eisinger et al. | 435/7.25 |
| 4,965,211 A | 10/1990 | Wieder et al. | 436/543 |
| 5,124,268 A | 6/1992 | Dakubu | 436/537 |
| 5,792,330 A | 8/1998 | Petersen et al. | 204/452 |
| 5,830,769 A | 11/1998 | Wieder et al. | 436/536 |
| 5,876,960 A | 3/1999 | Rosen | 435/39 |

(Continued)

FOREIGN PATENT DOCUMENTS

EP    03707656    2/2007

(Continued)

OTHER PUBLICATIONS

Beeby, A., et al., "Luminescence imaging microscopy and lifetime mapping using kinetically stable lanthanide (III) complexes", *Journal of Photochemistry and Photobiology*, B: Biology 57, pp. 83-89 (2000).

(Continued)

*Primary Examiner*—Ruth A Davis
*Assistant Examiner*—Sheridan R Macauley
(74) *Attorney, Agent, or Firm*—Steinfl & Bruno

(57) ABSTRACT

A method and an apparatus for detecting and quantifying bacterial spores on a surface. In accordance with the method: bacterial spores are transferred from a place of origin to a test surface, the test surface comprises lanthanide ions. Aromatic molecules are released from the bacterial spores; a complex of the lanthanide ions and aromatic molecules is formed on the test surface, the complex is excited to generate a characteristic luminescence on the test surface; the luminescence on the test surface is detected and quantified.

43 Claims, 12 Drawing Sheets

DPA-rich core.

U.S. PATENT DOCUMENTS

| | | | |
|---|---|---|---|
| 6,136,549 A | 10/2000 | Feistel | 435/7.1 |
| 6,242,268 B1 | 6/2001 | Wieder | 436/536 |
| 6,569,630 B1* | 5/2003 | Vivekananda et al. | 435/6 |
| 6,599,715 B1 | 7/2003 | Vanderberg et al. | 435/34 |
| 6,766,817 B2 | 7/2004 | da Silva | |
| 6,918,404 B2 | 7/2005 | da Silva | |
| 7,066,586 B2 | 6/2006 | da Silva | |
| 7,306,930 B2 | 12/2007 | Ponce | 435/34 |
| 2002/0135772 A1 | 9/2002 | Bornhop et al. | 356/450 |
| 2003/0064427 A1 | 4/2003 | Felkner et al. | 435/31 |
| 2003/0138876 A1 | 7/2003 | Ponce et al. | 435/34 |
| 2004/0014154 A1 | 1/2004 | Ponce et al. | 435/7.32 |
| 2005/0136508 A1 | 6/2005 | Ponce | 435/39 |
| 2006/0292664 A1 | 12/2006 | Ponce | 435/34 |
| 2007/0031916 A1 | 2/2007 | Ponce | 435/34 |
| 2007/0117175 A1 | 5/2007 | Ponce | 435/29 |

FOREIGN PATENT DOCUMENTS

| | | |
|---|---|---|
| WO | 00/63422 | 10/2000 |
| WO | 01/83561 | 11/2001 |
| WO | 01/83561 A | 11/2001 |
| WO | 03/024491 A2 | 3/2003 |
| WO | 03/067211 | 8/2003 |
| WO | WO 03/065009 | 8/2003 |
| WO | WO 03065009 A2 * | 8/2003 |

OTHER PUBLICATIONS

Beverly, M.B., et al., "Analysis of Dipicolinic Acid in Bacterial Spores by Electron Monochromator-Mass Spectrometry," *Presented at the 47th ASMS Conference on Mass Spectrometry and Allied Topics*, Dallas, Texas, 2 pages total (Jun. 13-17, 1999).

Branda, S., et al., "Fruiting body formation by *Bacillus subtilis*," *PNAS*, vol. 98, No. 20, 11621-11626 (Sep. 25, 2001).

"Bio-Threat Alert (BTA™) Strips," 1 page total (Spring 2001).

Gómez-Hens, A., et al., "Terbium-Sensitized Luminescence: A Selective and Versatile Analytical Approach," *Trends in Analytical Chemistry*, vol. 21, No. 2, pp. 131-141 (2002).

Hindle, A., et al., "Dipicolinic Acid (DPA) Assay Revisited and Appraised for Spore Detection," *Analyst*, vol. 124, pp. 1599-1604 (1999).

Horrocks Jr., W., et al., "Lanthanide Ion Luminescense Probes of the Structure of Biological Macromolecules", *American Chemical Society*, No. 14, pp. 384-392 (1981).

Koehler, T.M., "*Bacillus anthracis* Genetics and Virulence Gene Regulation," *Current Topics in Microbiology & Immunology*, vol. 271, pp. 143-164.

Lester, E., et al., "An Anthrax "Smoke" Detector", *IEEE Engineering in Medicine and Biology*, pp. 38-42 (Sep./Oct. 2002).

Lutterbach, M.T.S., et al., "Biofilm Formation on Brass Coupons Exposed to Cooling Water", *Brazilian Journal of Chemical Engineering*, vol. 14, No. 1 (Mar. 1997).

Lutterbach, M.T.S., et al., "Biofilm Formation Monitoring in an Industrial Open Water Cooling System," *Revista de Microbiologia*, 28, pp. 106-109 (1997).

Mitchell, A.C., et al., "Measurement of nanosecond time-resolved fluorescence with a directly gated interline CCD camera",Journal of Microscopy, vol. 206, Pt. 3, pp. 233-238 (Jun. 2002).

Murrel, W.G., "Chemical Composition of Spores" Chapter 7.

Nicholson, W.L., et al., "Resistance of Bacillus Endospores to Extreme Terrestrial and Extraterrestrial Environments", *Microbiology and Molecular Reviews*, vol. 64, No. 3, pp. 548-572 (Sep. 2000).

Paratamian, S.A., "Anthrax Detection, The Faster, The Better," *Microbiology 12*, Internet: <http://www.college.ucla.edu/webproject/micro12/honorprojects/Partamianp01/MicroHonorsWebPage.html> pp. 1-8 (Spring 2001).

Pastuska, J., et al., "Bacterial and fungal aerosol in indoor environment in Upper Silesia, Poland," *Atmospheric Environment*, 34, pp. 3833-3842 (2000).

Pierson, D., et al., "Microbial Contamination of Spacecraft", *Gravitational and Space Biology Bulletin* 14 (2) (Jun. 2001).

Rode, et al., "Induced Release of Dipicolinic Acid From Spores of *Bacillus megaterium*", *Journal of Bacteriology*, vol. 79, pp. 650-656 (1960).

Rose, L., et al., "Swab Materials and *Bacillus anthracis* Spore Recovery from Nonporous Surfaces", *Emerging Infectious Diseases*, vol. 10, No. 6, www.cdc.gov/eid (Jun. 2004).

Rosen, D.L., "Bacterial Endospore Detection Using Photoluminescence From Terbium Dipicolinate," *Reviews Analytical Chemistry*, vol. 18, No. 1-2, pp. 1-21 (1999).

Abstract of Scholl, P., et al., "Immunoaffinity Based Phosphorescent Sensor Platform for the Detection of Bacterial Spores," *Proceedings of the SPIE*, vol. 3913, 1 page total (2002).

Sacks, L.E., "Chemical Germination of Native and Cation-Exchanged Bacterial Spores with Trifluoperazine," *Applied and Environmental Biology*, vol. 56, No. 4, pp. 1185-1187 (1990).

Selvin, P.R., "The Renaissance of Flourescense Resonance Energy Transfer", *Natural Structural Biology*, vol. 7, No. 9, pp. 730-734 (2000).

Singh, R., "Microbial Diversity of Biofilms in Dental Unit Water System", *Applied and Environmental Microbiology*, pp. 3412-3420 (Jun. 2003).

Sorasaenee, K., et al., "Cooperative Binding of Tb(III) Supramolecular Complexes with Dipicolinic Acid: Improved Sensitivity of Metal-Contaning Lumophores in Biomedical Applications," *Division of Chemistry and Chemical Engineering*, California Institute of Technology, Pasadena, California, 1 page total (2003).

Uchida, I., et al., "Cloning and Characterization of a Gene Whose Product Is a trans-Activator of Anthrax Toxin Synthesis", *Journal of Bacteriology*, vol. 175, No. 17 (Sep. 1993).

Vaid, A., et al., "The destruction by microwave radiation of bacterial endospores and amplification of the released DNA", *Journal of Applied Microbiology*, vol. 85, pp. 115-122 (1998).

Vereb, G., et al., "Temporarily and Spectrally Resolved Imaging Microscopy of Lanthanide Chelates", Biophysical Journal, vol. 74, pp. 2210-2222 (May 1998).

Warth, A.D., "Liquid Chromatographic Determination of Dipicolinic Acid from Bacterial Spores," *Applied and Environmental Microbiology*, vol. 38, No. 6, pp. 1029-1033 (Dec. 1979).

Xiao, M., et al., "An improved instrument for measuring time—resolved lanthanide emission and resonance energy transfer", *Review of Scientific Instruments*, vol. 70, No. 10 (Oct. 1999).

Belgrader, et al., "A minisonicator to rapidly disrupt bacterial spores for DNA analysis", *Analytical Chemistry*, 71, pp. 4232-4236 (1999).

Branda, S., et al., "Fruiting body formation by *Bacillus subtilis*," *PNAS*, vol. 98, No. 20, 11621-11626 (Sep. 25, 2001).

Elbanowski, et al., "The Lanthanides Probes In Investigation Of Biochemical Systems", *Journal of Photochemistry and Photobiology A: Chemistry*, vol. 99, pp. 85-92 (1996).

Lamture, et al., Intensity Luminescent Immunoreactive Conjugates of proteins and Dipicolinate-Based Polumeric Tb (III) Chelates, Biconjugate Chemistry, vol. 6, pp. 88-92 (1995).

Pellegrino, P., et al., "Enhanced spore detection using dipicolinate extaction techniques", Analytica Chimicha Acta, vol. 455, No. 2, pp. 1667-177(Jan. 8, 2002).

Pellegrino, P.M., et al., "Bacterial endospore detection using terbium dipicolinate photoluminescence in the presence of chemical and biological materials", Analytical Chemistry 1998 U.S. Army Res. Lab, vol. 70, No. 9, pp. 1755 (1998).

Pierson, D., et al., "Microbial Contamination of Spacecraft", *Gravitational and Space Biology Bulletin* 14 (2) (Jun. 2001).

Scholl, P., et al., "Immunoaffinity based phosphorescent sensor platform for the detection of bacterial spores", Proc. SPIE Int Soc Opt Eng, Vaol.3913, pp. 204-214.

Seveus, et al., "Time-resolved fluorescence imaging of europheu label in immnunohistochemistry and in situ hybridization", Cytometry, 13. pp. 329-338 (1998).

PCT International Search Report for PCT/US03/03036 filed on Jan. 31, 2003 in the name of California Institute of Technology.

PCT International Search Report for PCT/US2006/022988 filed on Jun. 13, 2006 in the name of California Institute of Technology.

PCT Written Opinion for PCT/US2006/022988 filed on Jun. 13, 2006 in the name of California Institute of Technology, et al.

A. J. Alvarez, M. Khanna, G A. Toranzos, and G Stotzky, "Amplification of DNA bound on clay minerals," *Molecular Ecology*, vol. 7, pp. 775-778, 1998.

R. I. Amann, W. Ludwig, and K. H. Schleifer, "Phylogenetic Identification and in-Situ Detection of Individual Microbial-Cells without Cultivation," *Microbiological Reviews*, vol. 59,pp. 143-169, 1995.

Balzani V, Decola L, Prodi L, Scandola F: Photochemistry of Supramolecular Species. *Pure Appl Chem 1990*, 62:1457-1466.

Balzani V: Supramolecular Photochemistry. *Pure Appl Chem* 1990, 62:1099-1102.

D. L. Balkwill, F. R. Leach, J. T. Wilson, J. F. McNabb, and D. C. White, "Equivalence of Microbial Biomass Measures Based on Membrane Lipid and Cell-Wall Components, Adenosine-Triphosphate, and Direct Counts in Subsurface Aquifer Sediments," *Microbial Ecology*, vol. 16, pp. 73-84, 1988.

P. Belgrader. W. Benett, D. Hadley. I. Richards, P. Stratlon, R. Mariella and F. P. Milanovich, "Infectious disease-PCR detection of bacteria in seven minutes." *Science*, vol. 284. pp. 449-450, 1999.

P. Belgrader, C.I. Elkin. S.B, Brown. S.N. Nasarabadi, R.G. Langlois, F.P. Milanovich, B.W. Colston, and G.D. Marshall. "A reusable flow-through polymerase chain reaction instrument for the continuous monitoring of infectious biological agents," *Analyt. Chem.* vol. 75, pp. 3446-3450, 2003.

M. Carl. R. Hawkins, N. Coulson. I. Lowe. D.L. Robertson. W.M. Nelson, R.W. Titball and J.N. Woody. "Detection of spores of *Bacillus.anthracis* using the polymerase chain-reaction," *J. Infectious Diseases*, vol. 165, pp. 1145-1148. 1992.

A. Castro and R.T. Okinaka, "Ultrasensitive, direct detection of a specific DNA sequence of *Bacillus anthracis* in solution," *Analyst.* vol. 125. pp. 9-11, 1999.

B. D. Church and H. Halvorson, "Dependence of the Heat Resistance of Bacterial Endospores on Their Dipicolinic acid Content," *Nature*, vol. 183, pp. 124-125, 1959.

R. Connally, D. Veal, and J. Piper, "High resolution detection of fluorescently labeled microorganisms in environmental samples using time-resolved fluorescence microscopy," *Fems Microbiology Ecology*, vol. 41, pp. 239-245, 2002.

Enserink M: Anthrax: Biodefence Hampered by Inadequate Tests. *Science* 2001, 294:1266-1267.

J.W. Ezzell. T.G. Absbire. S.F. Little, B.C. Lidgerding. And C. Brown, "Identification of Bacillus-anthracis by using monoclonal-antibody to cell-wall antibody to cell-wall galacttose-N-acetylglucosamine polysaccharide," *J. Clin. Mlcrobiol*, vol. 28. pp. 223-231, 1990.

Grenthe I: Stability Relationships among the Rare Earth Dipicolinates. *Journal of the American Chemical Society* 1961, 83: 360-364.

W.D. Griffiths and G.A.L. Decosemo. "The assessment of bioaerosols—A critical- review," *J. Aerosol Sci.*. vol. 25, pp. 1425-1458. 1994.

W.D. Griffiths, I.W. Stewan. S.J. Futter, S.L. Upton, and D. Mark, The development of sampling methods for the assessment.

I. Henderson. C.J. Duggleby, and P.C.B. Turnbull. "Differentiation of *Bacillus-anthracis* from other *BacIllus-cereus* group bacteria with the Pcr," *Int. J. Systematic Bacteriol.*, vol. 44. pp. 99-105. 1994.

J. Ho, "Future of biological aerosol detection," *Analyrica Chimica Acta*, vol. 457, pp. 125-148, 2002.

P.M. Holland. R.D. Abramson, R. Watson. and D.H. Gelfand, "Detection of specific polymerase chain-reaction product by utilizing the 5'-3'exonuclease activity of thermus-aquaticus DNA-polymerase," in *Proc. Nat. Acad. Sci. USA*, vol. 88. 1991. pp. 7276-7280.

G. Horneck, H. Bucker, and G. Reitz, "Long-Term Survival of Bacterial-Spores in-Space," *Life Sciences and Space Research*), vol. 14, pp. 41-45, 1994.

W. D. Horrocks Jr., "Lanthanide Ion Luminescence in Coordination Chemistry and Biochemistry," in *Progress in Inorganic Chemistry*, vol. 31. New York: Wiley, 1984, pp. 1.

Hunnicutt, D. W., M. J. Kempf, and M. J. McBride. 2002. Mutations in *Flavobacteriumjohnsoniae gldF* and *gldG* disrupt gliding motility and interfere with membrane localization of GIdA. *J. Bacteriol*. 184: 2370-2378.

T.V. Inglesby, D.A. Henderson, J.G. Bartlett, M.S. Ascher. E. Eitzen, A.M. Friedlander, J. Hauer. J. McDade, M.T. OSterholm, T. O-Toole.

G. Parker, T.M.mPerl, P.K. Russell, and K. Tonat, "Anthrax as a biological weapon-Medical and public health management," *JAMA*, vol. 281, pp. 1735-1745. 1999.

K. Ito, K. Nakagawa, S. Murakami, H. Arakawa, and M. Maeda, "Highly sensitive simultaneous Bioluminescent measurement of acetate kinase and pyruvate phosphate dikinase activities using a firefly luciferase-luciferin reaction and its application to a tandem Bioluminescent enzyme immunoassay," *Analytical Sciences*, vol. 19, pp. 105-109, 2003.

F.W. Janssen, A.J. Lund. and L.E. Anderson, "Colorimetric assay for dipicolinic acid In bacterial spores," *Science*, vol. 127. pp. 26-27, 1958.

M. Johns. L. Harrington, R.W. Titball, and D.L. Leslie. "Improved methods for the detection of *Bacillus-anthracls* spores by the polymerase chain-reaction," *Lett. Appl. Microbiol*. vol. 18, pp. 236-238.1994.

J. G Jones, "Effect of Environmental-Factors on Estimated Viable and Total Populations of Planktonic Bacteria in Lakes and Experimental Enclosures," *Freshwater Biology*, vol. 7, pp. 67-91, 1977.

Kempf. M. J. and M. J. McBride. 2000. Transposon insertions in the *Flavobacterium johnsoniae ftsX* gene disrupt gliding motility and cell division. J. *Bacteriol*. 182: 1671-1679.

J. Knight, "US postal service puts anthrax detectors to the test," *Nature*, vol. 417, pp. 579-579, 2002.

L. J. Kricka, "Chemiluminescence and bioluminescence," *Analytical Chemistry*, vol. 71, pp. 305R-308R, 1999.

D.B. Lacy and R.J. Collier. "Structure and function of anthrax toxin," in *Anthrax, Current Topics* In *Microbiology and Immunology*, vol. 271, pp. 61-85, 2002.

D. Lawrence, S. Heitefuss, and H.S.H. Seifert, "Differentiation of *Bacillusanthracis* from *bacillus-cereus* by gas-chromatographic whole-cell fatty-acid analysis," *J. Clin. Mlcrobiol*. vol. 29, pp. 1S08-1512, 1991.

Lehn JM: Supramolecular Chemistry-Scope and Perspectives Molecules, Supermolecules, and Molecular Devices. *Angewandte Chemie-International Edition in English 1988*, 27:89-112.

Lester E et al: "A second-generation anthrax smoke detector" IEEE Engineering in Medicine and Biology Magazine, IEEE Service Center, Pisacataway, NJ, US, vol. 23, No. 1, Jan. 2004, pp. 130-135, XP001201545 ISSN: 0739-5175 the whole document.

N.A. Logan, J.A. Carman, I. Melling, and R.C.W. Berkeley. "Identification of *Bacillus-antbracis* by api tesIS," *J. Medical Microbial*. vol. 20. pp. 75-85, 1985.

A. Lundin, "Use of firefly luciferase in ATP-related assays of biomass, enzymes, and metabolites," *Bioluminescence and Chemiluminescence, Pt C*, vol. 305, pp. 346-370,2000.

R. L. Mancinelli and M. Klovstad, "Martian soil and UV radiation: microbial viability assessment on spacecraft surfaces," *Planetary and Space Science*, vol. 48, pp. 1093-1097, 2000.

G Manfredi, A. Spinazzola, N. Checcarelli, and A. Naini, "Assay of mitochondrial ATP synthesis in animal cells," *Methods in Cell Biology*. vol. 65, vol. 65, pp. 133-145, 2001.

McBride, M. J. And M. J. Kempf. 1996. Development of techniques for the genetic manipulation of the gliding bacterium *Cytophaga johnsonae*. J. *Bacteriol*. 178: 583-590.

A. C. Mitchell, J. E. Wall, J. G. Murray, and C.G. Morgan, "Direct modulation of the effective sensitivity of a CCD detector: a new approach to time-resolved fluorescence imaging," *Journal of Microscopy-Oxford*, vol. 206, pp. 225-232, 2002.

M. M. Moeseneder, J. M. Arrieta, G Muyzer, C. Winter, and G J. Herndl, "Optimization of terminal-restriction fragment length polymorphism analysis for complex marine bacterioplankton communities and comparison with denaturing gradient gel electrophoresis," *Applied and Environmental Microbiology*, vol. 65, pp. 3518-3525, 1999.

C. G Morgan and A. C. Mitchell, "Fluorescence lifetime imaging: An emerging technique in fluorescence microscopy," *Chromosome Research*, vol. 4, pp. 261-263, 1996.

W. Nicholson and P. Setlow; "Sporulation, germination and outgrowth," *Molecular biology methods for bacillus*, S. Cutting, Ed. Sussex, England: John Wiley and Sons, 1990, 391-450).

M. Paidhungat, B. Setlow, A. Driks, and P. Setlow, "Characterization of spores of *Bacillus subtilis* which lack dipicolinic acid," *Journal ofBacteriology*, vol. 182, pp. 5505-5512, 2000.

G. Patra, P. Sylvestre, V. Ramisse, I. Therasse, and IL. Guesdon. "Isolation of a specific chromosomic DNA sequence of *Bacillus anthracis and its possible use in diagnosis," Fems Immunol. Medical Microblol.*, vol. 15. pp. 223-231.1996.

A.P. Phillips and K.L. Martin. "Evaluation of a microfluorometer in Immunofluorescence assays of individual spores of*bacillus-anthracis* and *bacillus-cereus," J.ImnwntJlogical MetiuJdJ*, vol. 49, pp. 271-282. 1982.

A.P. Phillips, K.L. Martin, N.L. Cross, and R.G. Drake, "Evaluation of immunoradiometric and Elisa versions of a microtitre plate assay for *bacillusanlhracis* spores," *J. Immunological Merhod1*, vol. 70, pp. 75-81, 1984.

A.P. Phillips and K.L. Martin. "Quantitative immunofluorescenoe studies of the serology of *bacillus-anthracis* spores," *Appl. Environmenral Microbiol.*, vol. 46, pp. 1430-1432, 1983.

V. Ramisse, G. Patra. H. Garrigue. J.L. Guesdon, and M. Mock, "Identification and characterization of *Bacillus anthracis* by multiplex PCR analysis of sequences on plasmids pXO1 and pX02 and chromosomal DNA," *Ferns Microbiol. Lett.* vol. 145, pp. 9-16, 1996.

C. Redmond, M.J. Pearce, R.T. Manchee, and B.P. Berdal, "Deadly relic of the great war," *Nature*. vol. 393. pp. 747-748.1998.

Rosen DL, Sharpless C, McGown LB: Bacterial Spore Detection and Determination by Use of Terbium Dipicolinate Photoluminescence. *Anal Chem* 1997, 69: 1082-1085.

Rosen DL: Wavelength Pair Selection for Bacterial Endospore Detection by Use of Terbium Dipicolinate Photoluminescence. *Appl Optics* 1998, 37: 805-807.

Sabbatini N, Guardigli M, Lehn J M: Luminescent Lanthanide Complexes as Photochemical Supramolecular Devices. *Coord Chem Rev 1993*, vol. 123:201-228.

M. Schena, D. Shalon, R. W. Davis, and P. O. Brown, "Quantitative Monitoring of Gene-Expression Patterns with a Complementary-DNA Microarray," *Science*, vol. 270, pp. 467470, 1995.

Sinha S: *Systematics and the Properties of the Lanthanides*. Edited by Sinha S: NATO ASI Series 109; 1983.

P. Sneath, "Longevity of micro-organisms," *Nature*, vol. 195, pp. 643-646, 1962.

P.J. Stopa, "The flow cytometry of *Bacillus anthracis* spores revisited," *Cytometry*, vol. 41, pp. 237-244, 2000.

B.N. Strizhkov, A.L. Drobyshev, V.M. Mikhailovlch, and A.D. Mirzabekov, "PCR amplification on a microarray of gel-immobilized oligonucleotides: Deteclion of bacterial toxin- and drug-resistant genes and their mutations," *Biotechnique.*, vol. 29. pp. 844-??? 2000.

V. Torsvik, I. Goksoyr, and F. L. Daae, "High Diversity in DNA of Soil Bacteria," *Applied and Environmental Microbiology*, vol. 56, pp. 782-787, 1990.

P.C.B. Turnbull. "Definitive identification of *Bacillus anthsacis*—A review," *J. Applied Microbiol*, vol. 87. pp. 237-240. 1999.

M. Varughese, A.V. Teixeira, S.H. Liu. and S.H. Leppla. "Identification of a receptor-binding region within domain 4 of the protective antigen component of anthrax *toxin." Infection and Immunity*, vol. 67, pp. 1860-1865, 1999.

Venkateswaran, K., M. Kempf. F. Chen, M. Satomi, W. Nicholson, and R. Kern. 2003. *Bacillus nealsonii* sp. nov. isolated from a spacecraft assembly facility, whose spores are gamma-radiation resistant. *Int J. Syst. Evol. Microbiol.* 53 : 165-172.

G Vereb, E. Jares-Erijman, P. R. Selvin, and T. M. Jovin, "Temporally and spectrally resolved imaging microscopy oflanthanide chelates," *Biophysical Journal*, vol. 74, pp. 2210-2222, 1998.

R. H. Vreeland, W. D. Rosenzweig, and D. W. Powers, "Isolation of a 250 million-year old halotolerant bacterium from a primary salt crystal," *Nature*, vol. 407, pp. 897-900,2000.

D. C. White, W. M. Davis, J. S. Nickels, J. D. King, and R. J. Bobbie, "Determination of the Sedimentary Microbial Biomass by Extractable Lipid Phosphate," *Oecologia*, vol. 40, pp. 51-62, 1979.

U.S. Appl. No. 10/987,202, filed Nov. 12, 2004, Ponce.

Belgrader, et al, A minisonicator to rapidly disrupt bacterial spores for DNA analysis, Analytical Chemistry, 71, pp. 4232-4236 (1999).

Branda, S, et al, Fruiting body formation by *Bacillus subtilis, PNAS*, vol. 98, No. 20, 11621-11626 (Sep. 25, 2001).

Cable, Morgan L, et al, Bacterial Spore Detection by [Tb3+(macrocycle)(dipicolinate)] luminescence, *Beckman Institute, California Institute of Technology*, Pasadena, CA 91125, and In Situ Instruments Section, Jet Propulsion Laboratory, Pasadena, CA 91109 (2007).

Elbanowski, et al, The Lanthanides Probes in Investigation of Biochemical Systems, *Journal of Photochemistry and Photobiology A: Chemistry*, vol. 99, pp. 85-92 (1996).

Lamture, et al, Intensity Luminescent Immunoreactive Conjugates of proteins and oipicolinate-Based Polumeric Tb (III) Chelates, *Biconjugate Chemistry*, vol. 6, pp. 88-92 (1995).

McBride, at al, Autonomous Detection of Aerosolized *Bacillus anthracis* and *Yersinia pestis, Anal. Chemistry*, 2003 75, 5293-5299.

Pellegrino, P., et al, Enhanced spore detection using dipicolinate extaction techniques, *Analytica Chimicha Acta*, vol. 455, No. 2, pp. 1667-1677 (Jan. 8, 2002 ).

Pellegrino, P.M., et al, Bacterial endospore detection using terbium dipicolinate photoluminescence in the presence of chemical and biological materials, Analytical Chemistry 1998 U.S. Army Res. Lab, vol. 70, No. 9, pp. 1755 (1998).

Pierson, D., et al, Microbial Contamination of Spacecraft, *Gravitational and Space Biology Bulletin* 14 (2) (Jun. 2001).

Scholl, P. et al, Immunoaffinity based phosphorescent sensor platform for the detection of bacterial spores, Proc. SPIE Int Soc Opt Eng, vol. 3913 , pp. 204-214 (2000).

Seveus, et al., Time-resolved fluorescence imaging of europheu label in immnunohistochemistry and in situ hybridization, Cytometry, 13, pp. 329-338 (1998).

Slieman et al, Role of dipocolinic acid in survival of *bacillus subtilis spores exposed to artificial and solar UV radiation, Applied and Environmental Microbiology*, vol. 67, No. 3, 1274-1279, 2001.

Sorasaenee, K. et al, Cooperative Binding of Tb(III) Supramolecular Complexes with Dipicolinic Acid: Improved Sensitivity of Metal-Containing Lumophores in Biomedical Applications, *Division of Chemistry and Chemical Engineering, California Institute of Technology*, Pasadena, California, 1 page total (2003).

* cited by examiner

METHOD AND APPARATUS FOR DETECTING AND QUANTIFYING BACTERIAL SPORES ON A SURFACE

CROSS REFERENCE TO RELATED APPLICATIONS

This application claims priority to U.S. Provisional Ser. No. 60/740,805, for "A Rapid Single Spore Enumeration Assay" filed on Nov. 30, 2005, incorporated herein by reference in its entirety. This application is a continuation-in-part application of U.S. Ser. No. 10/987,202 filed on Nov. 12, 2004 which is incorporated herein by reference in its entirety. This application may also be related to U.S. Ser. No. 10/306,331 filed on Nov. 27, 2002 and U.S. Ser. No. 10/355,462 filed on Jan. 31, 2003, both of which are incorporated herein by reference in their entirety. The present application may also be related to U.S. Ser. No. 11/810,005 filed on Jun. 4, 2007, to U.S. Ser. No. 11/453,296, filed on Jun. 13, 2006, to U.S. Ser. No. 11/402,382 filed on Apr. 14, 2006.

STATEMENT OF GOVERNMENT SUPPORT

The present invention was made with support from the United States Government under Grant number NAS7-1407 awarded by NASA. The United States Government has certain rights in the invention.

BACKGROUND

1. Field

The present disclosure relates to the field of chemical detection. In particular, a method and apparatus for detecting and quantifying bacterial spores on a surface is disclosed.

2. Description of Related Art

Lanthanide complexes, particularly those of terbium ($Tb^{+3}$) and europium ($Eu^{+3}$), exhibit luminescence properties for the detection of aromatic biomolecules. The detection scheme is based on the absorption-energy transfer-emission mechanism, which is triggered by the binding of aromatic ligands to lanthanide complexes under UV excitation. Recent efforts have been focused on the detection of dipicolinic acid (DPA) (2,6-pyridinedicarboxylic acid), which is a unique constituent of bacterial spores present at high concentrations (up to 1 M). Dipicolinic acid is also a commercially available product having the following characteristics: CAS #: 499-83-2, Synonyms: 2,6 Pyridine Dicarboxylic Acid, Molecular Formula: $C_7H_5NO_4$, Molecular Weight: 167.12, Description: White crystalline powder, Sulphated Ash: 0.3% max, Moisture Content: 0.5% max, Melting Point: 242.0 to 245.0.degree. C., Assay: 99.0% min.

Bacterial spores are generally accepted to be indicator species for validating sterility since they are the most resilient form of life against sterilization regimens (Hindle and Hall, 1999 *Analyst*, 124, 1599-1604). Sterility testing of surfaces is traditionally performed by either (1) swabbing the surface with a cotton applicator, resuspending the swabbed spores, and plating the spore suspension onto growth media; or (2) using Replicate Organism Detection and Counting (RODAC) growth plates that are pressed against a surface to be analyzed. Each of these two bacterial spore assays requires 3-5 days before results are available.

As mentioned, dipicolinic acid (DPA) is present in high concentrations (about 1 molar or about 15% of by weight) in the core of bacterial spores (Murell, 1969, *Bact. Spore* 1, 216). In its deprotonated state, DPA is dipicolinate (DP) and is found in a 1:1 complex with $Ca^{2+}$ inside the spore, as shown in FIG. 1A. For all known life-forms, DPA is unique to bacterial spores and is naturally released into bulk solution upon germination—the process of spore-to-vegetative cell transformation. DP can also be released upon lysis of the bacterial spore. Thus, DPA and/or DP are indicator molecules for the presence of bacterial spores. DPA is a classic inorganic chemistry ligand that binds metal ions with high affinity. As mentioned, DPA takes the form of dipicolinate (DP) in its deprotonated form that binds to $Ca^{2+}$. DPA binding to terbium ions (or other luminescent lanthanide or transition metal ions) triggers intense green luminescence under UV excitation as shown in FIGS. 1B and 1C. The green luminescence turn-on signal indicates the presence of bacterial spores. The intensity of the luminescence can be correlated to the number of bacterial spores per milliliter.

U.S. patent application Publication No. 2003-0138876 for "Method bacterial endospore quantification using lanthanide dipicolinate luminescence" discloses a lanthanide that is combined with a medium to be tested for endospores. Dipicolinic acid released from the endospores binds the lanthanides, which have distinctive emission (i.e., luminescence) spectra, and are detected using photoluminescence. The concentration of spores is determined by preparing a calibration curve that relates emission intensities to spore concentrations for test samples with known spore concentrations. A lanthanide complex is used as the analysis reagent, and is comprised of lanthanide ions bound to multidentate ligands that increase the dipicolinic acid binding constant through a cooperative binding effect with respect to lanthanide chloride. The resulting combined effect of increasing the binding constant and eliminating coordinated water and multiple equilibria increases the sensitivity of the endospore assay by an estimated three to four orders of magnitude over prior art of endospore detection based on lanthanide luminescence.

U.S. patent application Publication No. 2004-0014154 for "Methods and apparatus for assays of bacterial spores" discloses a sample of unknown bacterial spores which is added to a test strip. The sample of unknown bacterial spores is drawn to a first sample region on the test strip by capillary action. Species-specific antibodies are bound to the sample when the unknown bacterial spores match the species-specific antibodies, otherwise the sample is left unbound. DPA is released from the bacterial spores in the bound sample. Terbium ions are combined with the DPA to form a Tb-DPA complex. The combined terbium ions and DPA are excited to generate a luminescence characteristic of the combined terbium ions and DPA to detect the bacterial spores. A live/dead assay is performed by a release of the DPA for live spores and a release of DPA for all spores. The detection concentrations are compared to determine the fraction of live spores. Lifetime-gated measurements of bacterial spores to eliminate any fluorescence background from organic chromophores comprise labeling the bacterial spore contents with a long-lifetime lumophore and detecting the luminescence after a waiting period. Unattended monitoring of bacterial spores in the air comprises the steps of collecting bacterial spores carried in the air and repeatedly performing the Tb-DPA detection steps above.

Exciting the combined terbium ions and DPA generates a luminescence characteristic of the combined terbium ions and DPA. This is achieved by radiating the combined terbium ions and DPA with ultraviolet light.

U.S. patent application Publication No. 2004-0014154 further discloses a method for live/dead assay for bacterial spores comprising the steps of: providing a solution including terbium ions in a sample of live and dead bacterial spores;

releasing DPA from viable bacterial spores by germination from a first unit of the sample; combining the terbium ions with DPA in solution released from viable bacterial spores; exciting the combined terbium ions and DPA released from viable bacterial spores to generate a first luminescence characteristic of the combined terbium ions and DPA to detect the viable bacterial spores; releasing DPA from dead bacterial spores in a second unit of the sample by autoclaving, sonication or microwaving; combining the terbium ions with the DPA in solution released from dead bacterial spores; exciting the combined terbium ions and DPA released from dead bacterial spores to generate a second luminescence characteristic of the combined terbium ions and DPA to detect the dead bacterial spores; generating a ratio of the first to second luminescence to yield a fraction of bacterial spores which are alive.

U.S. patent application Publication No. 2004-0014154 also discloses a method for unattended monitoring of bacterial spores in the air comprising the steps of collecting bacterial spores carried in the air; suspending the collected bacterial spores in a solution including terbium ions; releasing DPA from the bacterial spores; combining the terbium ions with DPA in solution; exciting the combined terbium ions and DPA to generate a luminescence characteristic of the combined terbium ions and DPA; detecting the luminescence to determine the presence of the bacterial spores; and generating an alarm signal when the presence of bacterial spores is detected or the concentration thereof reaches a predetermined magnitude.

Currently, bioburden levels are determined using the culture-depended methods, with which bacterial spores are quantified in terms of colony forming units (CFU's) that become visible on growth plates after incubation. There are several limitations for culture-dependent methods. First, this process requires 3-5 days to complete. Second, a large number of bacterial spores can aggregate on individual particulates giving rise to a single CFU, and thus a large underestimation of the bioburden. Third, colony-counting methods only account for cultivable spore-forming species, which constitute less than 1% in environmental samples.

It is desirable to provide a more efficient and sensitive method and apparatus for transferring all spore-forming bacteria (most especially bacteria of the genus *Bacillus* and *Clostridium*) originating on a surface, in the air or in water to a test surface, quantifying the spores, and further characterizing these spores as viable or nonviable.

SUMMARY

According to a first aspect of the present disclosure, a method is provided for detecting and quantifying individual bacterial spores comprising: capturing the bacterial spores; transferring the bacterial spores to a test surface; providing one or more lanthanide ions on the test surface; releasing aromatic molecules from the bacterial spores on the test surface; forming a complex of the one or more lanthanide ions and the aromatic molecules on the test surface; exciting the complex to generate a characteristic luminescence of the complex on the test surface; and detecting and quantifying the bacterial spores exhibiting the luminescence of the complex on the test surface.

According to a second aspect of the present disclosure, a method is provided for quantifying viable and nonviable bacterial spores comprising: capturing the bacterial spores; transferring the bacterial spores to a test surface; providing one or more lanthanide ions to the test surface; releasing aromatic molecules from the bacterial spores by germination of the bacterial spores on the test surface; forming a first complex of the one or more lanthanide ions and the aromatic molecules on the test surface; exciting the first complex to generate a characteristic luminescence of the first complex on the test surface; detecting and quantifying the bacterial spores exhibiting the luminescence of the first complex on the surface; releasing aromatic molecules from nongerminated spores on the test surface by lysis; forming a second complex of the one or more lanthanide ions and lysis-released aromatic molecules on the test surface; exciting the second complex to generate a characteristic luminescence of the second complex on the test surface; and detecting and quantifying the nonviable bacterial spores exhibiting the luminescence of the second complex on the test surface.

According to third aspect of the present disclosure, a method is provided for quantifying the percent viable spores in a mixed population of viable and nonviable bacterial pores comprising: transferring bacterial spores from a place of origin to a test surface comprising one or more lanthanide ions; inducing release of DPA/DP molecules from the transferred bacterial spores by germination; forming a first complex of the one or more lanthanide ions and the DPA/DP molecules; exciting the first complex with UV radiation; quantifying the luminescence of the first complex; subsequently inducing release of DPA/DP by lysis of non-germinated bacterial spores on the test surface; forming a second complex of the one or more lanthanide ions and lysis-induced DPA/DP molecules; exciting the second complex with UV radiation; quantifying the luminescence of the second complex; and dividing the quantified luminescence from the first complex by the sum of the luminescence of the first and second complexes.

According to a fourth aspect of the present disclosure, an apparatus is provided for detecting and quantifying bacterial spores comprising: an ultraviolet light radiation device to excite a complex of lanthanide ions and aromatic molecules and generate a characteristic luminescence of the complex; a microscope for detecting and quantifying bacterial spores exhibiting the luminescence of the complex; and an imaging device connected with the microscope for imaging the luminescence.

DETAILED DESCRIPTION

Transfer of Bacterial Spores from Place of Origin

Figure 1A:
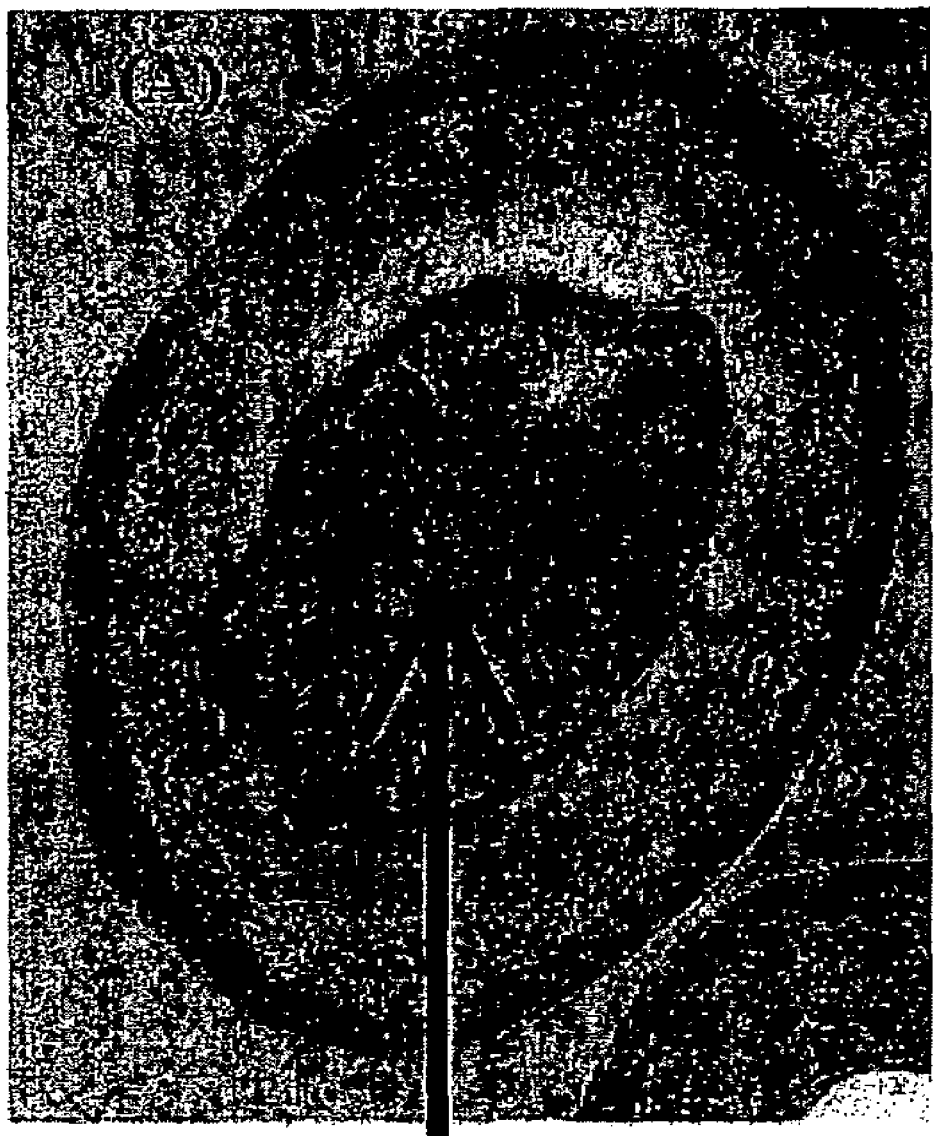
FIG. 1A is a microscopic image of a spore (about 1 μm in diameter) highlighting a DPA rich spore core.
Figure 1B:
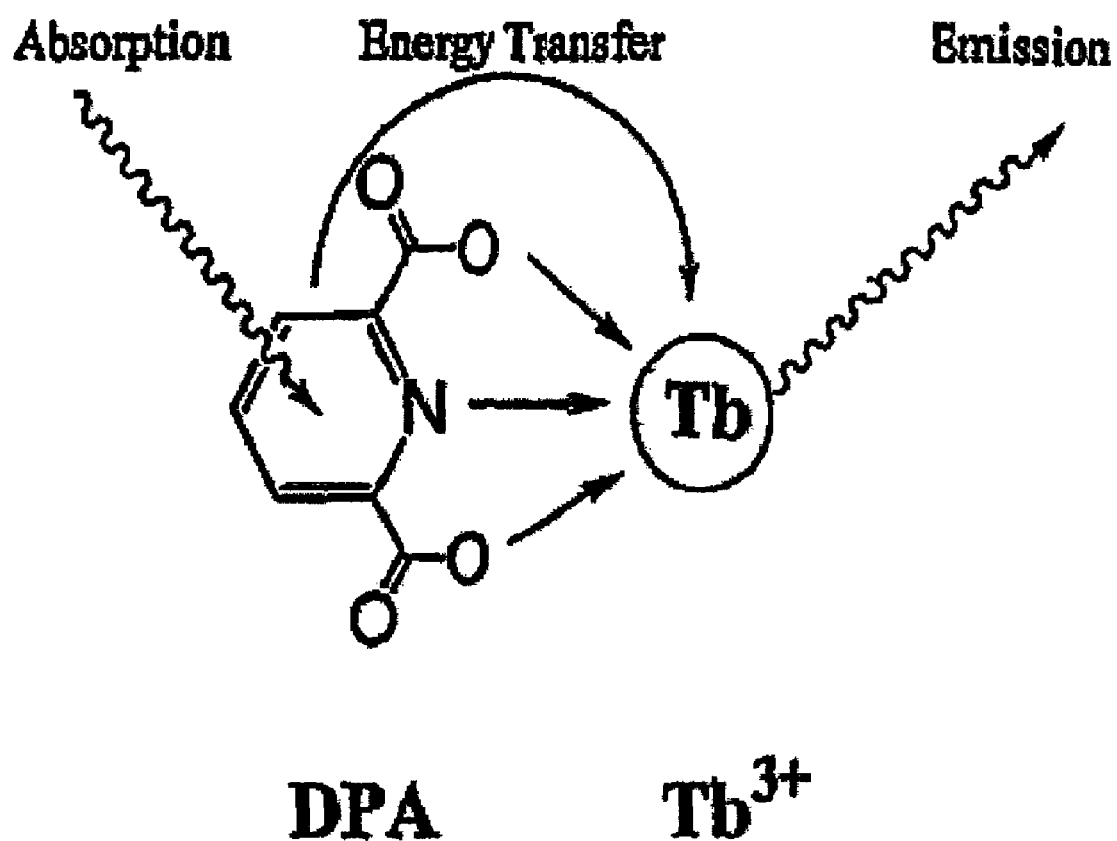
FIG. 1B is a diagram of a $Tb^{3+}$ ion (shaded ball) which by itself has a low absorption cross section ($<10$ $M^{-1}cm^{1}$) and consequently has low luminescence intensity. The $Tb^{3+}$ ion can bind the light harvesting DPA/DP (absorption cross section $>10^{4}M^{-1}cm^{-1}$) originating from the spore. DPA/DP binding gives rise to bright Th luminescence.
Figure 1C:
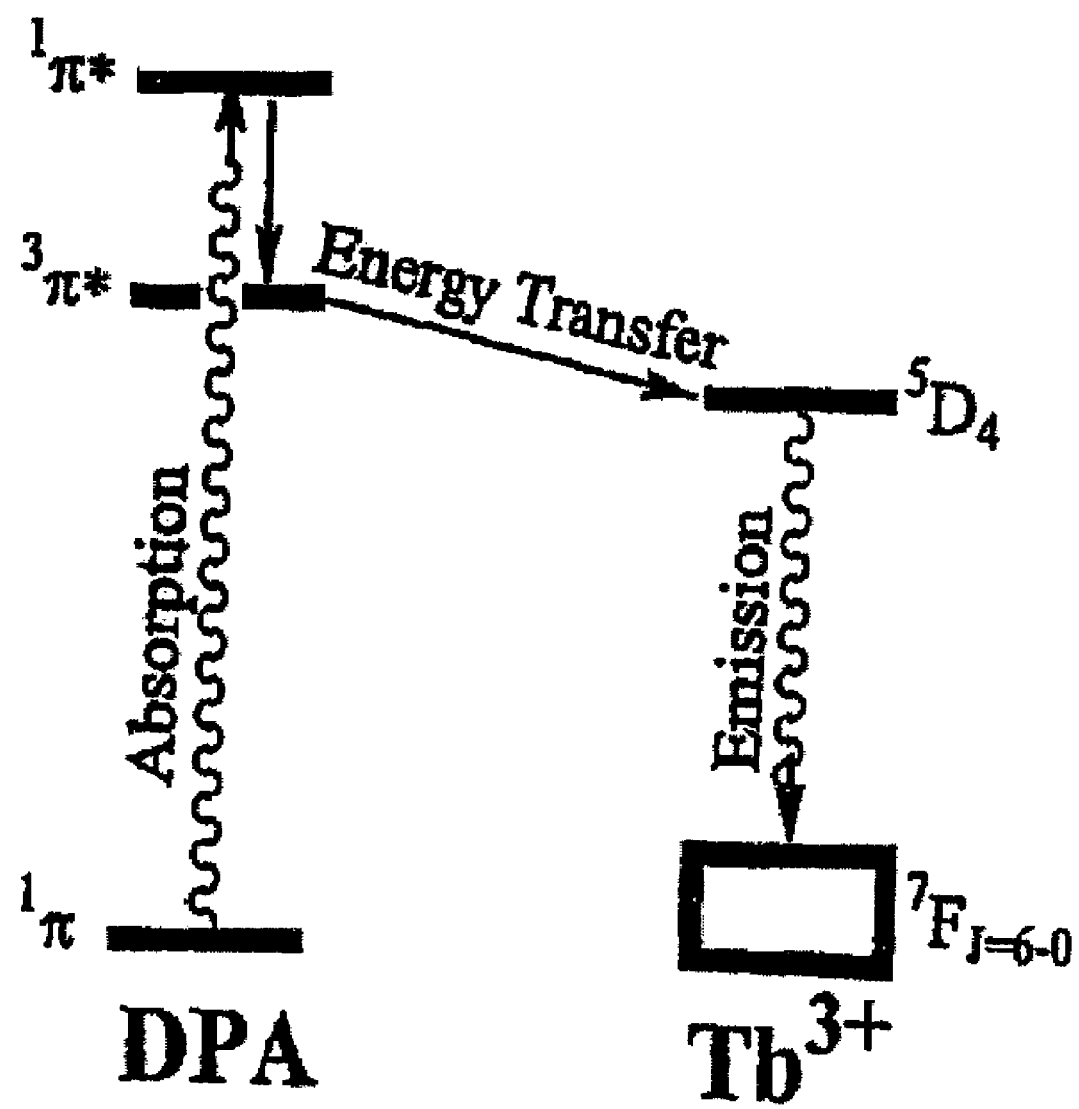
FIG. 1C is a diagram of a photophysical scheme for DPA/DP sensitized luminescence of the Tb-DPA complex (absorption-energy transfer-emission, AETE).
Figure 2A:
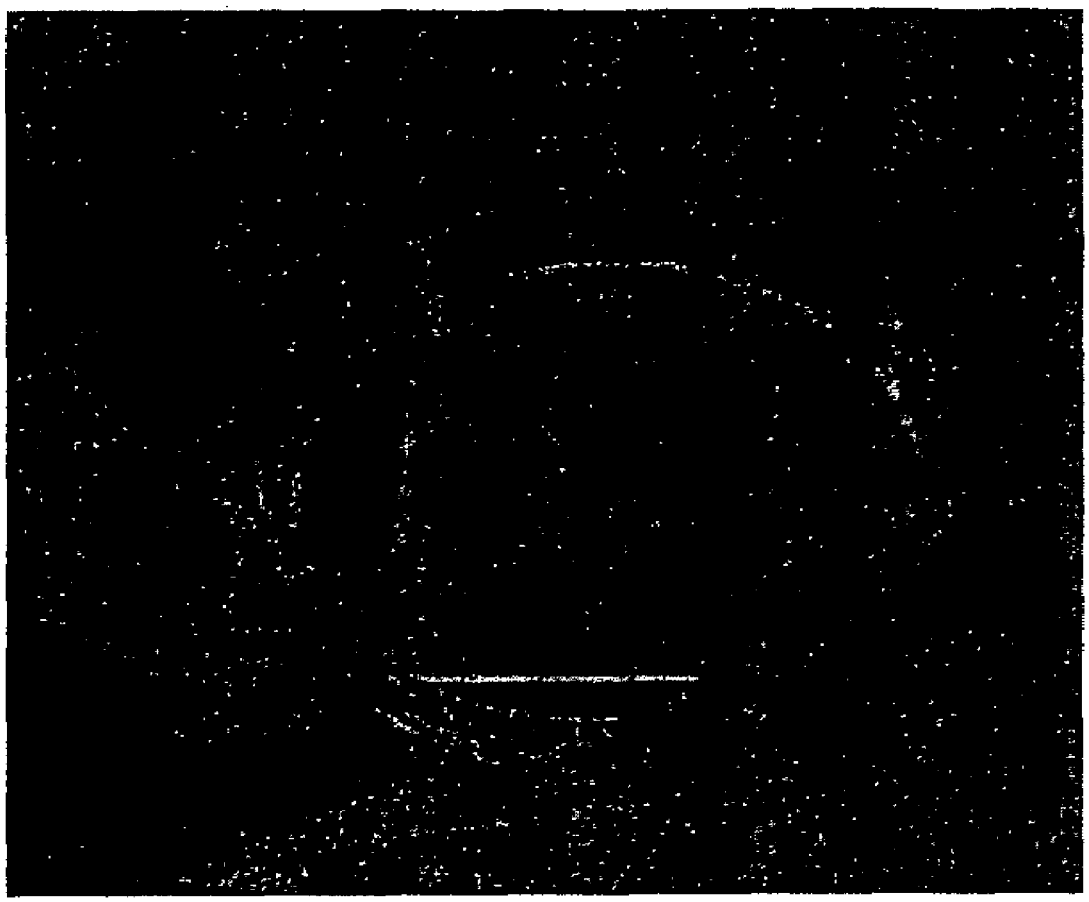
FIG. 2A is a photograph of a cotton swab being used to capture bacterial spores from a surface (Example 1).
Figure 2B:
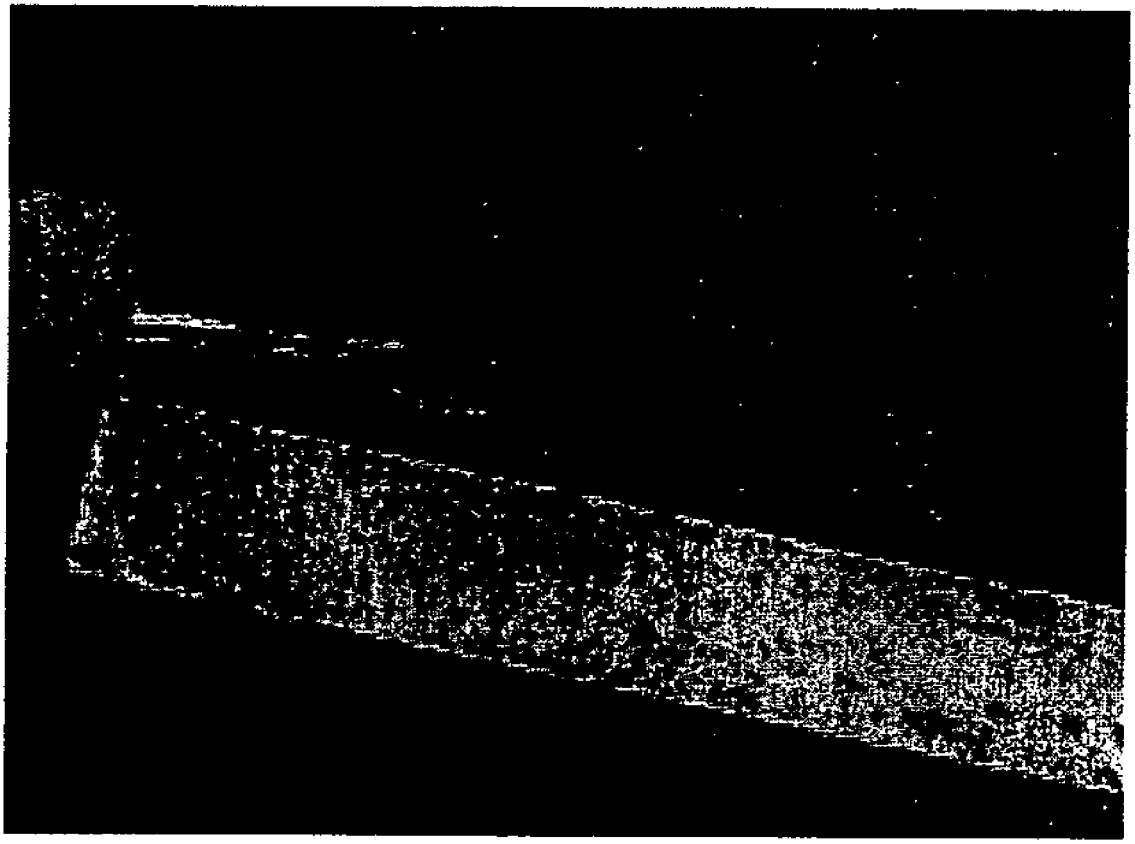
FIG. 2B is a photograph of PDMS polymer for capturing bacterial spores from surfaces (Example 1).

The lanthanide ion-DPA/DP luminescence assay can be employed to detect individual bacterial spores from a place of origin. DPA/DP refers to DPA and/or DP. In other words, DPA/DP means at least one between DPA and DP. A place of origin includes any solid surface, water and/or air. In order to posit the bacterial spores onto a test surface, the bacterial spores are first captured from a place of origin. A place of origin can include an infinite number of possibilities. Bacterial spores on solid surfaces are transferred from the solid surface onto a cotton swab (FIG. 2A), or an adhesive polymer, such as PDMS (polydimethyl siloxane) agar or agarose (FIG. 2B). Bacterial spores in water are transferred from water onto a water filter (e.g. membrane filter)(FIG. 2C). Bacterial spores in the air are transferred from the air onto an air filter (FIG. 2D). Examples of each of these types of transfer methods are described in Example 1.

The step of collecting bacterial spores carried in the air comprises capturing the bacterial spores with an aerosol sampler or impactor. Preferably, the step of collecting bacterial spores carried in the air comprises continuously sampling the air. In one embodiment, air is passed over quartz filter tape using an air sampler (Example 1). Alternatively, air can be passed over lanthanide-doped agar using an air sampler.

Test Surface

The test surface may be the same surface onto which the bacterial spores were transferred from the place of origin. In this case, a second transfer onto a test surface is not necessary. However, if the transferring surface is not to be the test surface, then the bacterial spores are transferred onto the test surface. The present invention provides a method of using a test surface on which bacterial spores are posited. Once the bacterial spores are located on the test surface, they can be induced to release DPA/DP by germination and/or physical lysis.

In one embodiment, the test surface contains an adhesive polymer. In another embodiment, the test surface contains (is "doped with") a germinating agent. In another embodiment, the test surface, onto which bacterial spores are transferred, contains (is "doped with") a lysing agent or is subjected to a method of lysis. In another embodiment, the test surface contains (is "doped with") lanthanide ions. In yet another embodiment, the test surface is transparent allowing for detection of the luminescence produced from the excited lanthanide-DPA complex. In a preferred embodiment, the test surface is an adhesive polymer (PDMS, agar, agarose) that contains a germinating agent, contains lanthanide ions, and is transparent, allowing for detection of lanthanide-DPA luminescence (FIG. 3). In a second preferred embodiment, the test surface is an adhesive polymer that contains a germinating agent, contains or is subjected to a lysing agent or method of lysis, contains lanthanide ions, and is transparent, allowing for detection of lanthanide-DPA luminescence. Alternatively, a test surface is an adhesive polymer that contains or is subject to a lysing agent or a method of lysis, contains lanthanide ions and is transparent, allowing for detection of lanthanide-DPA luminescence (FIG. 4).

According to one embodiment of the present disclosure, bacterial spores captured from a solid surface using cotton swabs can be transferred onto a test surface by resuspending the spores on the cotton swab into water, and then plating the water suspension onto a test surface. The bacterial spores on the cotton swab could also be suspended into water followed by filtration of the water suspension through a membrane water filter. The spores embedded onto the membrane water filter are then streaked onto a test surface (Example 1, 2). Alternatively, the membrane filter is the test surface. Alternatively, the swab is not made of cotton, but is made of any suitable material.

Examples of adhesive polymers include but are not limited to: polydimethyl siloxane (PDMS). Alternatively, agar can be doped with PDMS. Similarly, agarose can be doped with PDMS. In a preferred embodiment the adhesive polymer, PDMS, used to capture the bacterial spores from the surface of origin is subsequently used as a test surface. PDMS has low chemical activity, it is hydrophobic, it is optically transparent above 250 nm and it is impermeable to water. With these characteristics, a PDMS test surface allows for induction of lanthanide-DPA/DP luminescence, detection and quantifying. In one embodiment of the present disclosure, the test surface is optically transparent greater than 250 nm. In an alternative embodiment, the test surface is partially transparent.

In a second embodiment, the spores captured from a place of origin using an adhesive polymer are subsequently transferred from the adhesive polymer. This transfer can be carried out using several methods easily envisioned by one skilled in the art. For example, the spores can be streaked onto a test surface (Example 2).

In another embodiment, spores captured onto a membrane filter are transferred onto a test surface by a streaking method as disclosed in Example 2. Alternatively, spores on a membrane filter are physically lysed on the membrane filter and then pressed against an adhesive polymer such as PDMS containing lanthanide ions. Similarly, spores on a membrane filter can be streaked (Example 2) onto an adhesive polymer (e.g. PDMS, agar, agarose) that contains lanthanide ions and L-alanine for induction of germination. In another embodiment, the membrane filter embedded with the bacterial spores is used as the test surface.

The step of collecting bacterial spores carried in the air comprises capturing the bacterial spores with an aerosol sampler or impactor. Preferably, the step of collecting bacterial spores carried in the air comprises continuously sampling the air. In one embodiment, air is passed over quartz filter tape using an air sampler (Example 1). In one aspect the quartz filter tape is subsequently as the test surface. Alternatively, air can be passed over lanthanide-doped agar using an air sampler.

The agents used for germination and the agents used for lysing can be added to the test surface before or after the bacterial spores have been transferred onto the test surface.

Alternatively, the agents used for germination the agents used for lysing can be added in a mixture with the transfer of the bacterial spores. Examples of a germinating agent include but are not limited to: L-alanine, L-asparagine and D-glucose. Examples of lysing methods include but are not limited to: microwaving, plasma cleaning, dry heating, autoclaving, sonicating and hydrogen chloride gassing.

When the step of releasing DPA from the bacterial spores comprises microwaving the bacterial spores to heat the solution, the step of combining the lanthanide ions with the DPA in solution comprises cooling the heated solution to increase the fraction of bound lanthanide-DPA complex. One of skill in the art can envision several methods to prepare ("dope") the test surface for germination. Likewise, one of skill in the art can envision several methods to prepare ("dope") the test surface for lysing.

Lanthanide ions can be added to the test surface before the bacterial spores have been transferred onto said test surface, after the bacterial spores have been transferred onto said test surface, or in a mixture with the bacterial spores being transferred to the test surface. Lanthanide ions can be added before, after or in conjunction with the induced release of DPA/DP from the bacterial spores. Examples of lanthanide ions include, but are not limited to: terbium ($Tb^{3+}$), europium ($Eu^{3+}$) and dysprosium. In a preferred embodiment terbium ($Tb^{3+}$) ions are used.

Inducing the Lanthanide-DPA/DP Luminescence

A lanthanide ion-DPA/DP luminescence assay can be employed to detect individual bacterial spores on surfaces. For example, the lanthanide-DPA/DP luminescence assay can be combined with an optically transparent, adhesive polymer (PDMS, agar or agarose) to collect bacterial spores from surfaces to be tested. Once the bacterial spores are located on the test surface, they can be induced to release their DPA/DP content by germination (e.g. using L-alanine) or physical lysis, for example by autoclaving or microwaving. The highly concentrated DPA/DP from the spores spills into the surrounding area, generating a high concentration region around the spore body. The reagents used for detection and induction of germination, if that is the chosen method for DPA/DP release, can be added into the matrix before or after the spores are sampled. The lanthanide-DPA/DP luminescence arising from the region around the spore body is then imaged onto a camera. The bacterial spore regions manifest themselves as bright spots that can be counted. Due to the long-lived excited states of luminescent lanthanides, lifetime-gated detection enables any fluorescent background from interferences to be eliminated. Lifetime gating drastically reduces the background and enables much greater contrast between the lanthanide-DPA/DP luminescence regions and the background.

It is understood by one skilled in the art, that upon release of DPA and/or DP outside the bacterial spore, the DPA and/or DP molecules can interact with other substances in its environment, resulting in a derivative of DPA or DP.

The step of detecting the luminescence to determine the presence of the bacterial spores comprises monitoring the luminescence with a spectrometer or fluorimeter, and the step of detecting the luminescence to determine the presence of the bacterial spores comprises continuously monitoring the luminescence.

In one embodiment of the present invention, an adhesive polymer for the terbium-DPA/DP luminescence assay for bacterial spores on surfaces is polydimethyl siloxane (PDMS) doped with $TbCl_3$ and L-alanine. The L-alanine induces germination to release the DPA/DP from the core of the spore to the immediate surroundings. The $TbCl_3$ binds the DPA/DP, which triggers green luminescence (543.5 nm) under UV excitation (250-300 nm) that can be quantified with a photodetector. Individual germinating spores can be imaged within a microscope field of view using a lifetime-gated camera.

From the perspective of sensor design, the bacterial spore is essentially a 1 μm sphere containing about $10^9$ molecules of DPA. In previous experiments (U.S. patent Pub No. 2004-0014154), spores were collected from surfaces using the standard cotton swabbing method, resuspended into water, and DPA/DP was then released into a bulk solution by germination or physical lysing and a subsequent lanthanide (Tb)-DPA luminescence assay was performed. This approach led to very dilute DPA solutions (e.g., 1 spore per ml of solution yields [DPA]=1 μM), which ultimately limits the sensitivity. As disclosed in the present invention, spores collected using the cotton swab can be suspended into water, and the water suspension can then be plated onto a testing surface for subsequent DPA/DP release, lanthanide-DPA/DP complexing, excitation, lumination and quantification. Alternatively, the water suspension can be filtered through a membrane filter and the spores on the filter can be streaked onto a testing surface.

Figure 3:
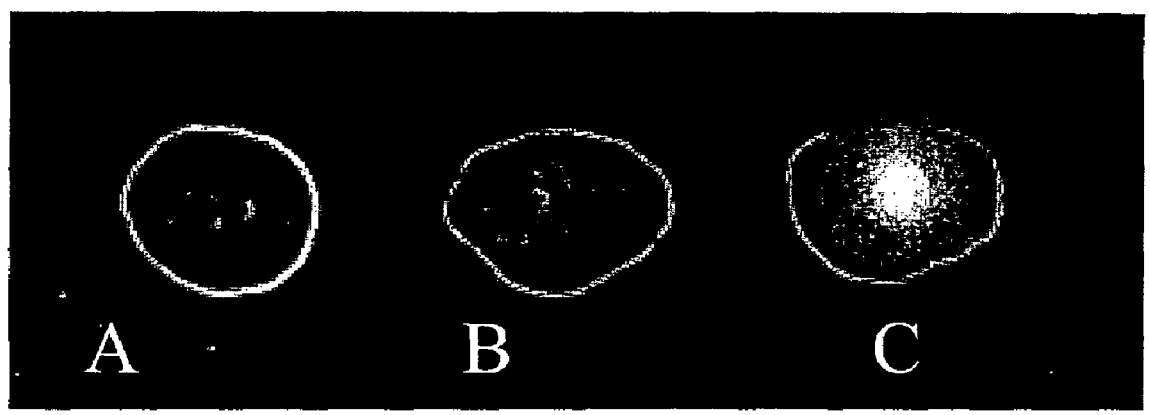
FIG. 3 depicts a photograph of a backlight illuminated quartz slide with three solidified agar drops. (A) No $Tb^{3+}$ added. (B) $Tb^{3+}$ added but no L-alanine (C) $Tb^{3+}$ and L-alanine added with photograph taken after germination was complete.

The traditional culture-based assays require 3 days for colonies to grow and be counted. This traditional culture-based assay, also known as the NASA standard assay, is reported in colony forming units (CFU), since the quantification is based on the number of colonies. However, a significant fraction of bacterial spores can undergo stage-1 germination, during which DPA (i.e., the chemical marker that is unique to bacterial spores) is released, in less than 4 minutes. This type of quantification, is reported as germinating spore units (GSU). Experimental results shown herein (Table 1) show a comparison of the GSU calculated following the teachings disclosed in this application, versus the CFU calculation of the NASA standard assay for the same amount of starting spores (total spore units/TSU). FIG. 3 further shows an L-alanine induced germination of *Bacillus subtilis* spores on a $TbCl_3$ doped agar. The DPA/DP released upon germination luminesces when complexed with the $Tb^{3+}$ ions. (Example 2).

Detection, Imaging and Quantification of lanthanide-DPA/DP Luminescence

A salient feature of the present disclosure is the implementation of lifetime-gated imaging to obtain an image with good contrast of bacterial spores after germination and/or lysis. Fluorescence lifetime imaging uses special detectors and light source technology to generate images wherein the contrast is related to the fluorescence lifetime across a sample. Lifetime gating takes advantage of the fact that lanthanide ion (e.g. terbium) luminescence lifetimes are on the order of milliseconds, while fluorescence lifetimes from impurities generally are on the order of nanoseconds. Lifetime gating drastically reduces the chance of false negatives, which could arise if the lanthanide ion luminescence is masked by background fluorescence from impurities.

More specifically, the imaging method takes advantage of the fact that a bacterial spore is essentially a 1 μm diameter bag comprising $10^8$ molecules of DPA and/or DP. Releasing DPA/DP by thermal lysis or germination in the presence of lanthanide ions generates local high lanthanide-DPA/DP concentrations (in the millimolar range) with correspondingly high luminescence intensities. When the luminescence "halo" surrounding the spore body is imaged into individual lifetime-gated CCD detector elements, individual spores will be easily counted. Even when spores are clustered together, the spore counts per cluster will be proportional to the intensity arising from a cluster. Thus, the resultant "bright spots" or "halos" are counted and the number of spores per bright spot is estimated by the luminescence of the spot (i.e. the spot intensity). The lifetime gating allows imaging of the long-lived lanthanide-DPA/DP excited state in the presence of short-lived fluorescence interferences (impurities, etc).

Under UV (blacklight) illumination, the luminescence of the embedded $Tb^{3+}$ ions increased dramatically upon germination within 40 minutes of the bacterial spores, while the embedded $Tb^{3+}$ luminescence in the control sample that had no exposure to L-alanine remained weak (FIG. 3). An agar control sample without $Tb^{3+}$ that was covered with bacterial spores also did not yield detectable luminescence. Note that the bright edges of the spots are artifacts of drying due to refraction from accumulated material, which would not appear in a lifetime-gated image.

Figure 4:
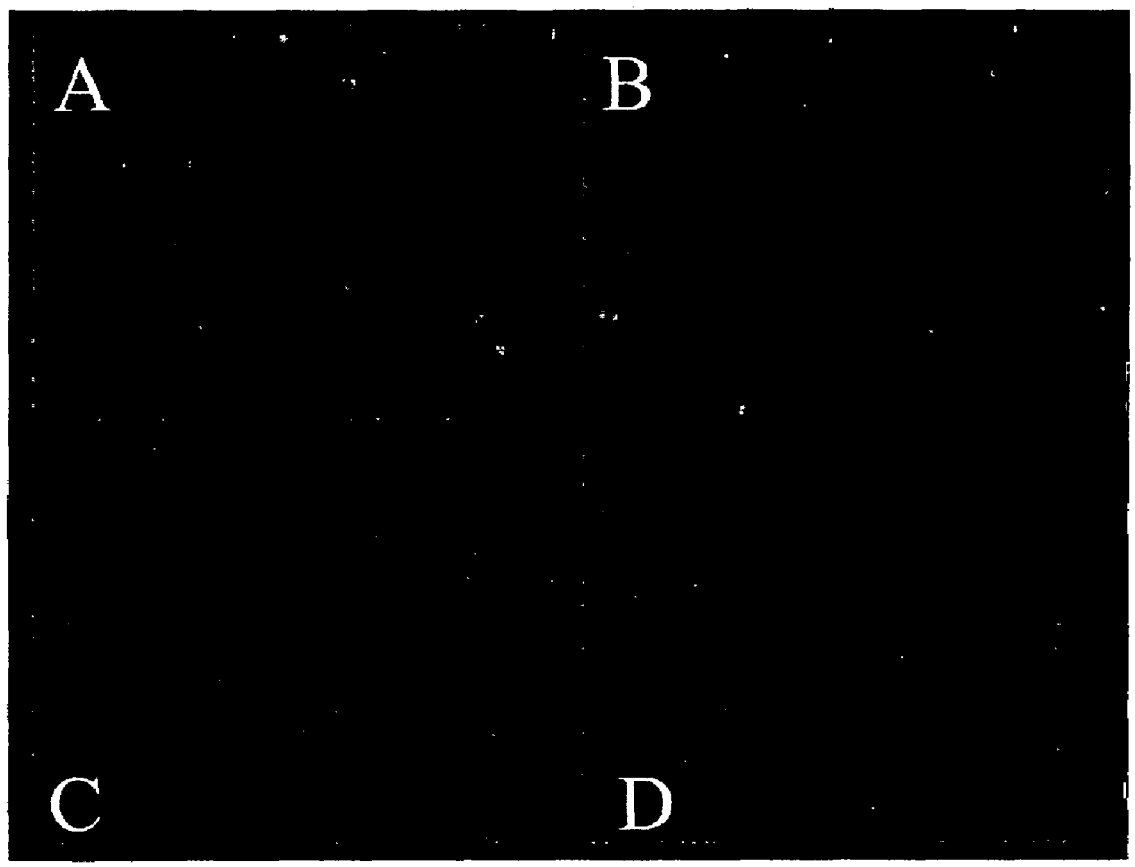
FIG. 4 depicts four 1 mm thick pieces of PDMS inoculated with *B. subtilus* spores. (A) Plasma cleaned and placed onto $Tb^{3+}$-doped agar (B) Plasma cleaned and placed onto $Tb^{3+}$-doped agar. (C) Not plasma cleaned, placed onto $Tb^{3+}$-doped agar. (D) Not plasma cleaned, place onto $Tb^{3+}$-doped agar.

An example of imaged Th-DPA/DP complex representing spores on a PDMS test surface containing $Tb^{3+}$ ions, which were subsequently lysed using plasma cleaning are shown in FIG. 4. Those spores that were not subject to plasma cleaning, and thus did not lyse and release DPA/DP, did not exhibit fluorescence (panel C and D of FIG. 4).

Figure 5:
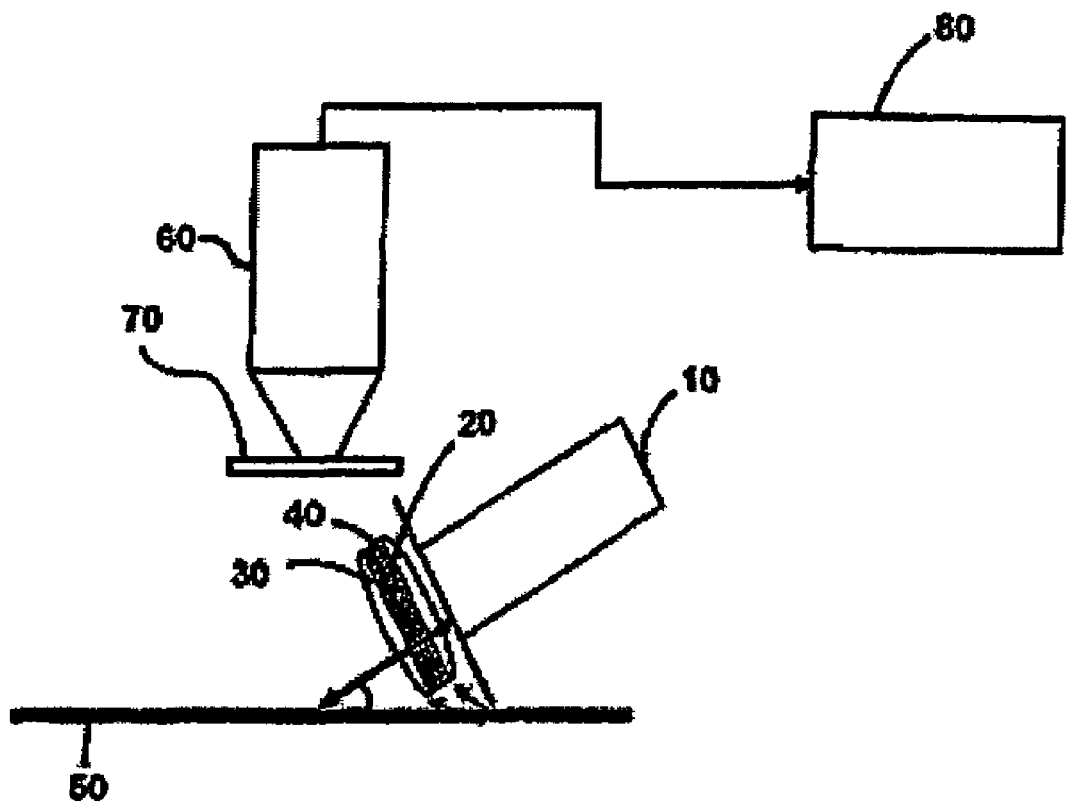
FIG. 5 depicts a schematic apparatus for imaging quantifying and counting of bacterial spores (Example 3).

The pictures in FIG. 3 were taken without magnification, and thus the individual spores cannot be enumerated as they germinate. However, the present disclosure provides germinating bacterial spores imaged with a lifetime-gated microscope (FIG. 5, Example 3). As the spores germinate, DPA is released from the core to generate high, localized DPA/DP concentrations, which show up as bright green luminescent halos surrounding the spore body. These results demonstrate that viable bacterial spores on surfaces can be enumerated (quantified) according to methods of the present invention. In another embodiment, viable and nonviable bacterial spores on surfaces are enumerated according to the method of the present invention. In a further embodiment, viable and/or nonviable spores on surfaces are enumerated according to the disclosed device of the present invention.

Figure 6:
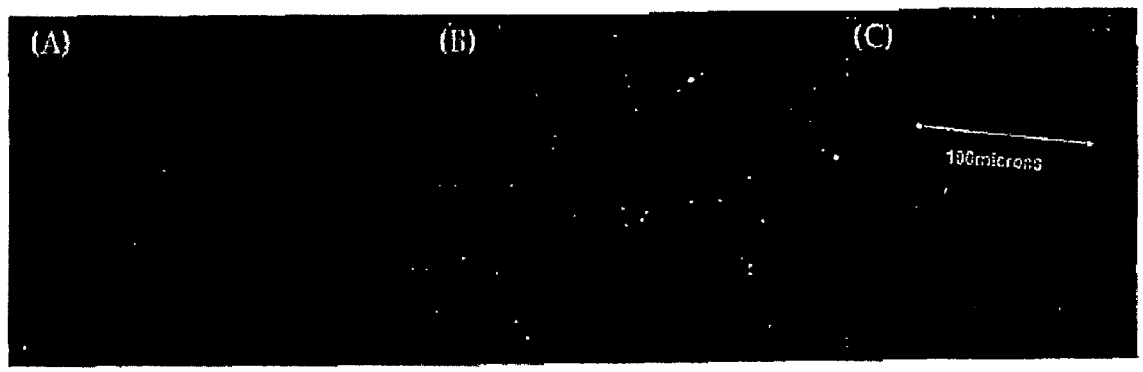
FIG. 6 depicts $Eu^{3+}$ microspheres (1 μm) on fluorescent paper imaged with an ImageX-TGi gated CCD camera mounted on a Carl Zeiss fluorescence microscope with 40-times objective, excited with a 300 Hz Perkin Elmer flashlamp. Images are obtained (A) without gating, (B) with gating (100 μs delay, 2.7 μs gate), and (C) 100 μm reference graticule to estimate spatial resolution.

FIG. 6 shows lifetime-gated images of $Eu^{3+}$ microspheres on highly fluorescent paper obtained with an Imagex-TGi lifetime-gated CCD camera mounted on a Carl Zeiss fluorescence microscope with 40× objective, excited with a 300 Hz Perkin elmer flashlamp (Example 3). $Eu^{3+}$ microspheres were employed because they are commercially available and have analogous photophysical properties. The ImageX system effectively rejected all of the strong background fluorescence when a delay time of 100 μs was used. The present invention allows for microspheres exhibiting weak, long-lived luminescence immobilized on a highly fluorescent matrix to be imaged with high contrast against a silent background when gating is applied.

Figure 7:
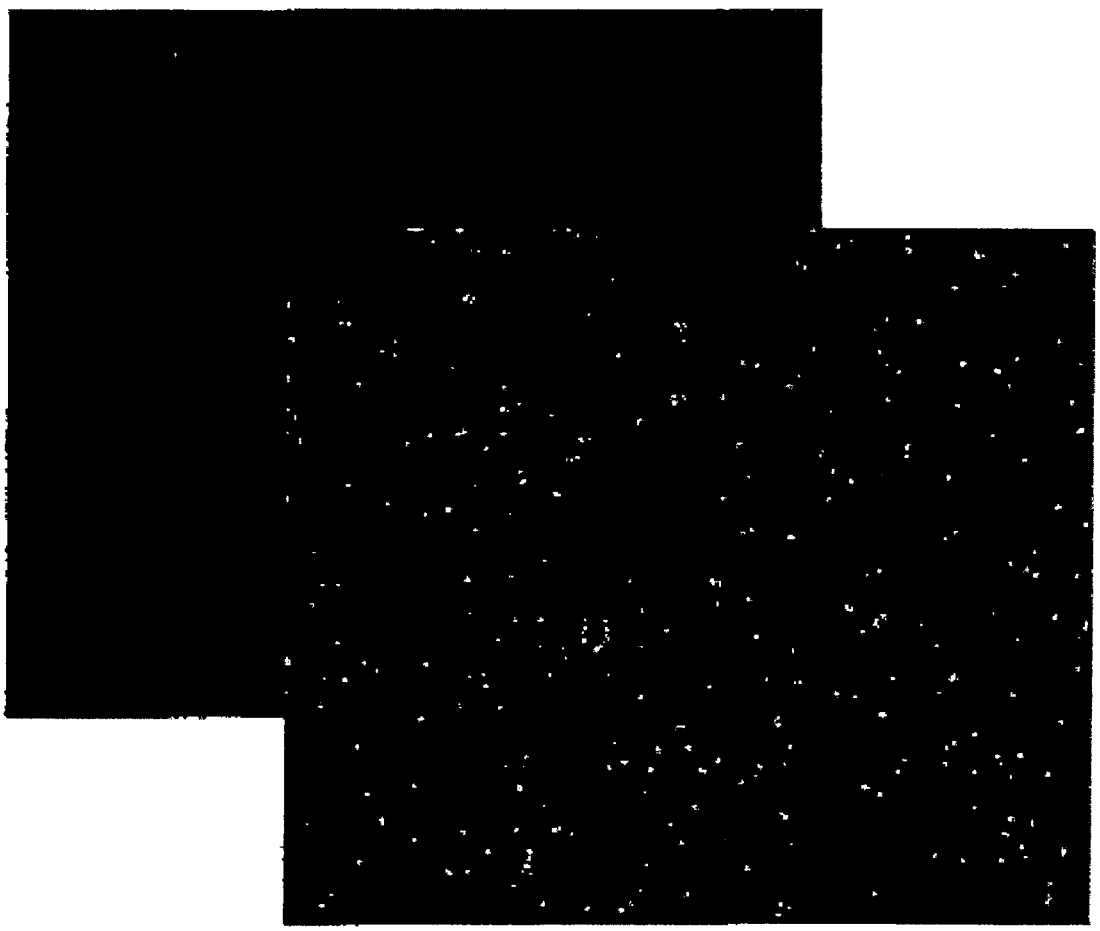
FIG. 7 depicts two lifetime-gated photographs showing bacterial spores on R2A agar before germination (left portion of the figure) and after germination (right portion of the figure).

Another example of the invention is illustrated in FIG. 7. Bacterial spores were added onto the surface of R2A agar doped with 10 mM L-alanine (Example 1) to induce germination and 100 μM $TbCl_3$ to generate bright luminescent spots around the spore body as they germinated and released DPA/DP. A Xe-flash lamp firing at 300 Hz with a 275 nm interference filter provided excitation for the Tb-DPA complex, and the corresponding bright spots from the bacterial spore Tb-DPA luminescent halos were imaged with a lifetime-gated camera set at a delay time of 100 μs and an integration time of 2 ms. The individual bacterial spores become clearly visible as countable spots after germination. The images shown in FIG. 7 can be obtained by an apparatus as shown in FIG. 5. The apparatus of FIG. 5 comprises: 1) an ultraviolet light radiation device 10 (e.g., a Xenon flash lamp); 2) a first elliptical lens 20 and a second elliptical lens 30; 3) The light radiation device 10 and the lenses 20, 30 (40 represents the space in between the lenses) can have a 45 degrees inclination with respect to a stage or test surface 50 where the bacterial spores are located. The distance between lens 30 and stage 50 can be one inch. The distance between light radiation device 10 and stage 50 can be two inches. The light radiation device 10 is adapted to excite a complex of one or more lanthanide ions and aromatic molecules and generate a characteristic luminescence of the complex; 4) a microscope 60 for detecting and quantifying bacterial spores exhibiting the luminescence of the complex. 5) A red bandpass filter 70, suitable for Eu3+, can be connected with the microscope 60; 6) an imaging device 80 (e.g., a nanoCCD camera) connected with the microscope 60.

Quantifying Viable Bacterial Spores

Instead of diluting the DPA/DP into bulk solution, bacterial spores can be immobilized onto a test surface such as an adhesive polymer (e.g., PDMS, agar with PDMS, agarose with PDMS), and then induced to germinate or lyse on the polymer test surface to generate local high DPA/DP concentrations (i.e, DPA and/or DP remains in the immediate surroundings of the spore body). To obtain viable counts, germination is induced by doping L-alanine (or other germination inducing agents) into the polymer matrix; lanthanide ions (e.g. $TbCl_3$) also doped into the polymer, allow for imaging and quantification of bacterial spores by triggering luminescence in the presence of DPA/DP. To obtain total counts, the bacterial spores immobilized on the polymer test surface containing lanthanide ion are physically lysed (e.g., by dry heating, microwaving, sonication, plasma cleaning, hydrogen chloride gassing or autoclaving) and the subsequent fluorescence emitted upon excitation of the lanthanide-DPA/DP complex is imaged and quantified resulting in the total number of live and dead bacterial spores.

The present disclosure also provides a method and apparatus to measure the fraction of bacterial spores that remain viable or alive, hence a live/dead assay for bacterial spores. The method combines dipicolinic acid/dipicolinate-triggered lanthanide luminescence and DPA/DP release from (1) viable bacterial spore through germination, and (2) DPA/DP release subsequent to lysis of all viable and nonviable bacterial spores. The ratio of the results from steps (1) to the sum of steps (1) and (2) yield the fraction of bacterial spores that are alive.

In one embodiment of the present disclosure, a method is provided for quantifying the percentage of viable spores in a population mixture of viable and inviable spores. In a preferred embodiment, the method for quantifying the percent viable spores in a mixed population of viable and inviable spores comprises transferring bacterial spores from their place of origin onto a test surface containing lanthanide ions, inducing germination of DPA/DP from the transferred bacterial spores, exciting the lanthanide-DPA/DP complex with UV radiation, quantifying the luminescence associated with the lanthanide-DPA/DP of germination, subsequently lysing the non-germinated bacterial spores on the test surface, exciting the lysis-induced lanthanide-DPA/DP complex with UV radiation, and quantifying the luminescence associated with the lanthanide-DPA/DP of lysis. Using the same test surface for germination and subsequent lysis allows for an accurate calculation of the percent viable spores in any given mixed population of viable and non-viable spores. The ability to rapidly quantify the fraction of viable bacterial spores from various origins (e.g. solid surfaces, water and air) is an essential feature of the present invention.

The method and apparatus of the present disclosure provide the imaging of the spherical resolution of the high concentrating region of DPA (the "halo") around each spore body, which has been germinated or lysed. The present method makes it possible to detect and quantify extremely low concentrations of bacterial spores in very short time. The method and apparatus for bacterial spore detection and quantification according to the present disclosure yields results within minutes and requires approximately an hour for quantifying the percent viability of bacterial spores on surfaces.

Bioburden testing is an assessment of the numbers and types of microorganisms present on a product, and may be used to support sterilization validations. Sterility determination for surfaces are required by the pharmaceutical, health care, and food preparation industries for compliance with bioburden standards as outlined by USP, FDA, PDA, and AAMI.

TABLE 1

Results from experiments performed according to Examples 1-3

Surface Sampling: Swab Rinse

1540 TSU/cm$^2$
710 GSU/cm$^2$
120 CFU/cm$^2$
Ratio of GSU/CFU: 3.38

Water Sampling:

$5.0 \times 10^4$ TSU/cm$^2$
$3.4 \times 10^4$ GSU/cm$^2$
$1.2 \times 10^4$ CFU/cm$^2$
Ratio of GSU/CFU: 2.83

Air Sampling:

0.05 GSU/l of air
0.01 CFU/l of air
Ratio of GSU/CFU: 5.0

TSU: Total Spore Units
GSU: Germinating Spore Units
CFU: Colony Formation Units

While several illustrative embodiments have been shown and described in the above description, numerous variations and alternative embodiments will occur to those skilled in the art. Such variations and alternative embodiments are contemplated, and can be made without departing from the scope of the invention as defined in the appended claims.

EXAMPLE 1

Bacterial Spore Capture/Transfer Methods

Capture from solid surfaces: (FIG. 2A,B) For capture of bacterial spores from solid surfaces, adhesive polymer polydimethylsiloxan (PDMS) was used, purchased from Dow Corning. D2A agar (Difco) was also used in the capture of bacterial spores from solid surfaces. Cotton swabbing of solid surfaces: cotton swabs with bacterial spores were either suspended into water and plated onto testing surface, or water suspension of spores was filtered onto 0.2-µm membrane filter and then transferred onto test surface by "streaking" (Example 2) (See Table 1).

Figure 2C:
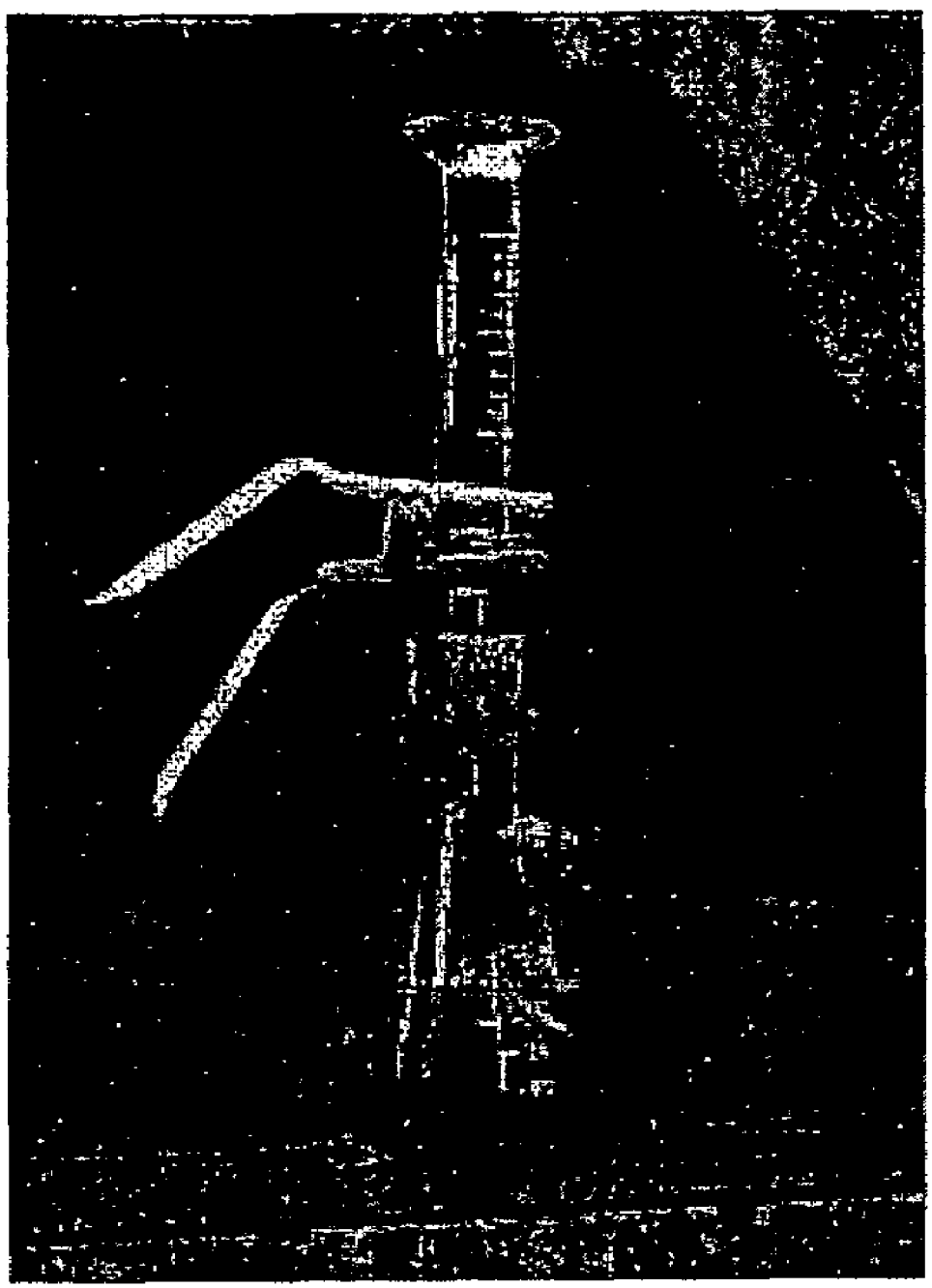
FIG. 2C is a photograph of a water filter for capturing bacterial spores from water (Example 1).

Capture from water: (FIG. 2C) For capture of bacterial spores from water a 0.2-µm membrane filter was used (Millipore). One of skill in the art can envision several mechanisms for separating and collecting bacterial spores from water using variations on the disclosed membrane water filter discussed above. Transfer of spores from filter to a testing surface is done by "streaking" (Example 2) (See Table 1).

Figure 2D:
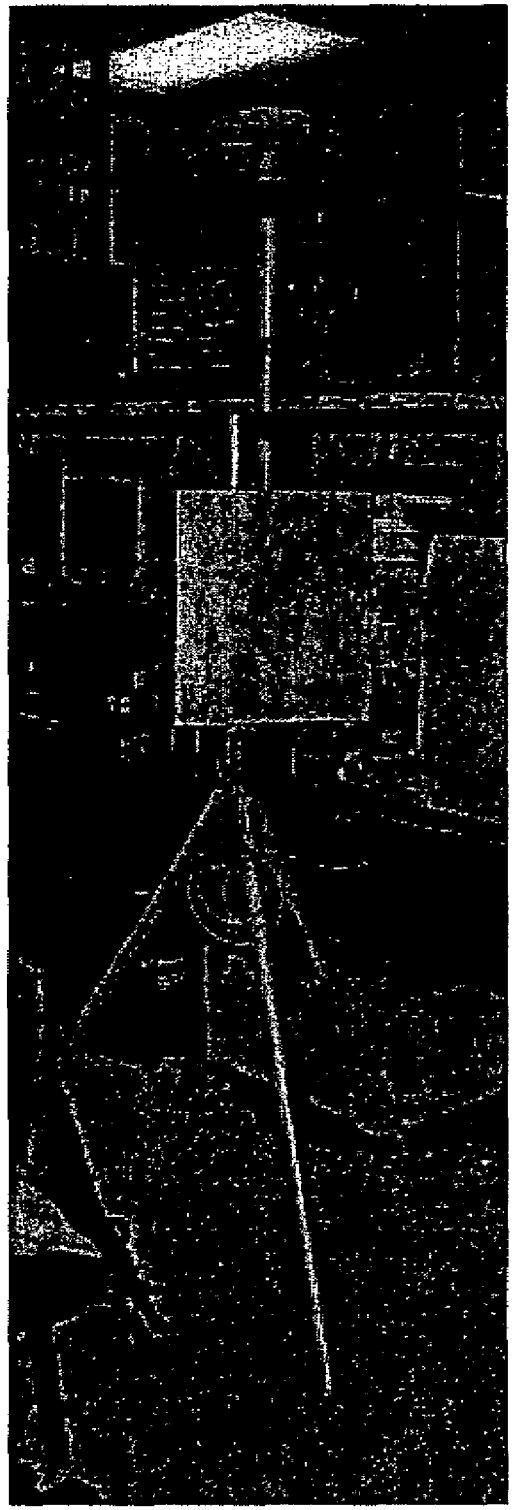
FIG. 2D is a photograph of an air filter as described herein for capturing bacterial spores from air. (Example 1).

Capture from air: (FIG. 2D) For capture of bacterial spores from air, quartz filter tape (Whatman) is used in combination with an air sampler (Bioscience International: SAS Super 100/180/360). The quartz filter tape is then suspended in water, and the water suspension is then plated onto the testing surface, or the water suspension is filter through a membrane filter which is then streaked onto the testing surface. Alternatively, the quartz filter can be used as the test surface (See Table 1).

Bacterial spores: Bacillus (*Bacillus subtilis*, *Bacillus cereus*, *Bacillus atrophaeus* etc.) spores from American Type Culture Collection (ATCC) were used in the examples provided herein. Stock solutions of purified endospores were prepared according to methods well known in the art. Plating of suspended spores was carried out by methods well known in the art (W. Nicholson and P. Setlow, "Sporulation, germination and outgrowth," *Molecular biology methods for bacillus*, S. Cutting, Ed. Sussex, England: John Wiley and Sons, 1990, 391-450).

EXAMPLE 2

Test Surface

"Streaking": Spores on the surface of a membrane filter are transferred to a test surface by contacting the two surfaces at one end and dragging across to the other end to effect the transfer of spores from a membrane onto a test surface. This process is referred to as "streaking". Alternatively spores on an adhesive polymer such as PDMS can also be streaked from the polymer onto a test surface.

Bacteria spores were immobilized onto a test sample surface of thin, flexible, clear, adhesive polymer polydimethylsiloxan (PDMS) (Dow Corning). PDMS was doped with L-alanine (Aldrich) to induce germination and generate local high concentration of DPA/DP. TbCl$_3$ (Aldrich) was also doped into the PDMS sample. The bacterial spores immobilized on the L-alanine and TbCl$_3$-containing polymer were physically lysed by microwave irradiation (Vaid and Bishop, 1998?), wherein DPA/DP was released and luminescence was turned on.

The test surface in FIG. 3 was prepared by adding 100 µl of R2A agar (doped with 1 mM TbCl$_3$ onto a quartz slide and allowing it to solidify. On top of the agar, 10 µl of 10$^9$ spores/ml *Bacillus subtilis* spores were added (i.e., 10$^7$ spores), followed by 10 µl of 1-mM L-alanine to induce germination.

The test surface in FIG. 4 shows fours 1 mm thick flat pieces of PDMS inoculated with *B. subtilus* spores. The PDMS pieces shown in panel A and B were placed into a plasma cleaner for 30 minutes. The pieces shown in panel C and D were not. Each of the four pieces were then placed onto Tb$^{3+}$-doped agar. The two plasma cleaned pieces produced bright spots corresponding to DPA/DP released from the *B. subtilus* spores during the plasma cleaning which complexed with the Tb$^{3+}$ ions in the agar. The two non-lysed PDMS test pieces did not produce bright spots because the *B. subtilus* spores on these pieces were not induced to release DPA/DP.

EXAMPLE 3

Detection and Quantifying, apparatus

An apparatus for detecting and quantifying bacterial spores on a surface including lanthanide ions and aromatic molecules released from the bacterial spores on the surface. The apparatus in FIG. 5 comprises a UV-light radiation device for exciting a complex of a Tb$^{3+}$ ion and DPA/DP to generate a characteristic luminescence of the complex on a surface. The source for the UV-light was a Xenon flash lamp, which was approximately 5 cm away the test surface. Between the Xenon flash lamp and the test surface were two C-amount elliptical lenses. The Xenon flash lamp and the test substrate were positioned at an angle of 45 degrees to each other. The area of irradiation by the Xenon flash lamp was observed by a microscope objective with a red bandpass filter suitable for $Eu^{3+}$ for detecting and quantifying bacterial spores exhibiting the luminescence of the complex on the surface. The image was transferred from the microscope to the imaging device for imaging bacterial spores exhibiting the luminescence, using an imageX nanoCCD camera (Photonic Research Systems Ltd, United Kingdom). The pixel size on the camera is 11.6 microns horizontal by 11.2 microns vertical and the camera has a chip with 752×582 pixels on a 10.25 mm×8.5 mm vertical area. Lifetime gated images were captured with a 100-μs delay integrating for 2 milliseconds. 6 to 13 images were taken over different areas of the medium. Each image captured an actual agarose area of 3.2 $mm^2$ at 40× magnification. The spatial resolution is a function of the camera, the camera objective and the microscope camera port. The microscope image is projected onto the camera port that then determines the spatial resolution.

The invention claimed is:

1. A method for detecting and quantifying individual bacterial spores comprising:

capturing the bacterial spores;

transferring the bacterial spores to a test surface;

providing one or more lanthanide ions on the test surface;

releasing aromatic molecules from the bacterial spores on the test surface;

forming a complex of the one or more lanthanide ions and the aromatic molecules on the test surface;

exciting the complex to generate a characteristic luminescence of the complex on the test surface; and detecting and quantifying the individual bacterial spores by imaging the bacterial spores via luminescence spots surrounding the bacterial spores, said luminescent spots generated on the test surface through lifetime-gated imaging, with a micrometric spatial resolution.

2. The method according to claim 1, wherein the capturing of the bacterial spores comprises transferring bacterial spores from a second surface by way of an adhesive polymer.

3. The method of claim 2, wherein the adhesive polymer is selected from the group consisting of PDMS, agar and agarose.

4. The method of claim 1, wherein the capturing of the bacterial spores comprises transferring bacterial spores from a second surface by way of a swab.

5. The method of claim 4, further comprising transferring the bacterial spores from the swab into water.

6. The method of claim 5 wherein the water is passed through a water filter.

7. The method of claim 1 wherein the capturing of the bacterial spores is from a place of origin selected from the group consisting of water and air.

8. The method of claim 7 wherein the transferring of the bacterial spores is from a place of origin to a filter selected from the group consisting of an air filter and a water filter.

9. The method of claim 1, wherein the test surface comprises at least one adhesive polymer selected from the group consisting of PDMS, agar, agarose, PDMS together with agar, and PDMS together with agarose.

10. The method of claim 1, wherein the test surface comprises at least one partially transparent adhesive polymer.

11. The method of claim 1, wherein the one or more lanthanide ions are provided to the test surface prior to the bacterial spores, after the bacterial spores, or as a mixture with the bacterial spores.

12. The method of claim 1, wherein the one or more lanthanide ions are terbium or europium or a mixture thereof.

13. The method of claim 1, wherein the aromatic molecules are selected from the group consisting of dipicolinic acid, dipicolinate, and dipicolinic acid together with dipicolinate.

14. The method of claim 1, wherein the aromatic molecules interact with the test surface resulting in a derivative of the aromatic molecules.

15. The method of claim 1, wherein the aromatic molecules are released from the bacterial spores by germination of the bacterial spores.

16. The method of claim 15, wherein the germination of the bacterial spores is induced by way of a germinating agent selected from the group consisting of L-alanine, L-asparagine and D-glucose.

17. The method of claim 1, wherein the aromatic molecules are released from the bacterial spores by lysis of the bacterial spores.

18. The method of claim 17, wherein the lysis of the bacterial spores is induced by way of a method of lysis selected from the group consisting of microwaving, autoclaving, sonication, plasma cleaning dry heating and hydrogen chloride gasing.

19. The method of claim 9 wherein the test surface further comprises at least one lanthanide ion and a germinating agent.

20. The method of claim 9 wherein the test surface further comprises at least one lanthanide ion and is subject to a method of lysis.

21. The method according to claim 1, wherein the complex is excited by UV light.

22. The method of claim 2 wherein the adhesive polymer is the test surface.

23. The method of claim 3 wherein the adhesive polymer is the test surface.

24. The method of claim 8, wherein the filter is the test surface.

25. The method of claim 1, wherein the releasing of aromatic molecules from the bacterial spores on the test surface is by germination of the bacterial spores on the test surface;

wherein the complex is a first complex;

wherein the method further comprises:

releasing aromatic molecules from nongerminated spores on the test surface by lysis;

forming a second complex of the one or more lanthanide ions and lysis-released aromatic molecules on the test surface;

exciting the second complex to generate a characteristic luminescence of the second complex on the test surface; and detecting and quantifying the bacterial spores by imaging the bacterial spores, via the luminescence of the second complex on the test surface by lifetime-gated imaging.

26. The method of claim 25 wherein the test surface comprises terbium or europium ions;

wherein the aromatic molecules are DPA and/or DP molecules;

wherein the exciting of the first and second complex is with UV radiation;

the method further comprising the step of dividing the quantified luminescence of the first complex by the sum of the luminescence of the first and second complexes.

27. A method of claim 26 wherein the quantifying of the bacterial spores represented by the generated luminescence comprises counting the number of luminescent spots and the number of spores per luminescent spot can be estimated by the spot intensity.

28. An apparatus for detecting and quantifying individual bacterial spores according to the method of claim 1, comprising:
   a test surface, wherein the test surface comprises one or more adhesive polymers, one or more lanthanide ions, bacterial spores and aromatic molecule released from said bacterial spores
   an ultraviolet light radiation device adjacent to the test surface to excite a complex of lanthanide ions and aromatic molecules and generate a characteristic luminescence of the complex;
   an life-time gated imaging device for imaging the luminescence.

29. An apparatus of claim 28 wherein a microscope is connected to the life-time gated imaging device.

30. A method for detecting and quantifying bacterial spores comprising:
   providing the bacterial spores on a test surface, each bacterial spore having a spore body;
   providing one or more lanthanide ions on the test surface;
   releasing aromatic molecules from the spore body of a bacterial spore onto the test surface, the released aromatic molecules defining on the test surface a surrounding area around the spore body of the bacterial spore;
   forming a complex of the one or more lanthanide ions and the aromatic molecules on the surrounding area;
   exciting the complex to generate a characteristic luminescence of the complex on the surrounding area; and
   detecting and quantifying the bacterial spores by imaging surrounding areas through lifetime-gated imaging with a micrometric spatial resolution.

31. The method of claim 30, wherein imaging surrounding areas is performed by imaging individual surrounding areas.

32. The method of claim 30, wherein imaging surrounding areas is performed by imaging surrounding areas of individual spores clustered together on the test surface.

33. The method of claim 30, wherein the bacterial spores are embedded in the test surface.

34. The method of claim 30, wherein the test surface is an adhesive polymer.

35. The method of claim 34 wherein the adhesive polymer is optically transparent.

36. The method of claim 30, wherein the releasing of aromatic molecules from the bacterial spores on the test surface is by germination of the bacterial spores on the test surface; and wherein the complex is a first complex;
   wherein the method further comprises:
   releasing aromatic molecules from nongerminated spores on the test surface by lysis the released aromatic molecules defining on the test surface a surrounding area around the spore body;
   forming a complex of the one or more lanthanide ions and the aromatic molecules on the surrounding area;
   exciting the complex to generate a characteristic luminescence of the complex on the surrounding area; and
   detecting and quantifying the bacterial spores by imaging surrounding areas through lifetime-gated imaging.

37. A method for detecting and quantifying bacterial spores, the method comprising
   providing the bacterial spores, each bacterial spore having a spore body;
   providing one or more lanthanide ions;
   releasing aromatic molecules from the spore body
   forming a complex of the one or more lanthanide ions and the aromatic molecules;
   exciting the complex to generate a characteristic luminescence of the complex; and
   detecting and quantifying bacterial spores by imaging the bacterial spores through lifetime-gated imaging,
   wherein
   releasing aromatic molecules from the spore body is performed on a test surface to generate on the test surface an aromatic molecules concentration region around the spore body
   the complex of the one or more lanthanide ions and the aromatic molecules is formed on said region, and
   detecting and quantifying bacterial spores is performed by imaging the aromatic molecules concentration regions on the test surface with a micrometric spatial resolution.

38. The method of claim 37, wherein the imaged aromatic molecules concentration regions are individual aromatic molecules concentration regions.

39. The method of claim 37, wherein the imaged aromatic molecules concentration regions are aromatic molecules concentration regions of individual bacterial spores clustered together on the test surface.

40. The method of claim 37, wherein the bacterial spores are embedded in the test surface.

41. The method of claim 37, wherein the test surface is an adhesive polymer.

42. The method of claim 41, wherein the adhesive polymer is optically transparent.

43. The method of claim 37, wherein the releasing of aromatic molecules from the bacterial spores on the test surface is by germination of the bacterial spores on the test surface; and wherein the complex is a first complex;
   wherein the method further comprises:
   releasing aromatic molecules from nongerminated spores on the test surface by lysis to generate on the test surface aromatic molecules concentration regions around each spore body;
   forming a second complex of the one or more lanthanide ions and lysis-released aromatic molecules on said concentration regions;
   exciting the second complex to generate a characteristic luminescence of the second complex on the concentration regions; and
   detecting and quantifying the bacterial spores by imaging the aromatic molecules concentration regions on the test surface.

* * * * *